United States Patent
Guo et al.

(10) Patent No.: US 9,616,126 B2
(45) Date of Patent: Apr. 11, 2017

(54) COMPOSITION, METHOD, AND KIT FOR ALPHA-1 PROTEINASE INHIBITOR

(71) Applicant: Grifols Therapeutics Inc., Research Triangle Park, NC (US)

(72) Inventors: Jianxin Guo, Clayton, NC (US); Anthony Klos, Raleigh, NC (US); Bret Coldren, Research Triangle Park, NC (US); Deborah Barnette, Cary, NC (US); Mark Manning, Research Triangle Park, NC (US)

(73) Assignee: Grifols Therapeutics, Inc., Research Triangle Park, NC (US)

( * ) Notice: Subject to any disclaimer, the term of this patent is extended or adjusted under 35 U.S.C. 154(b) by 0 days.

(21) Appl. No.: 14/926,450

(22) Filed: Oct. 29, 2015

(65) Prior Publication Data

US 2016/0106843 A1    Apr. 21, 2016

Related U.S. Application Data

(63) Continuation of application No. 13/504,783, filed as application No. PCT/US2010/055135 on Nov. 2, 2010, now abandoned.

(Continued)

(51) Int. Cl.
*A61K 9/19*    (2006.01)
*A61K 31/195*  (2006.01)
(Continued)

(52) U.S. Cl.
CPC .......... *A61K 47/183* (2013.01); *A61K 9/0019* (2013.01); *A61K 9/19* (2013.01); *A61K 31/185* (2013.01); *A61K 31/195* (2013.01); *A61K 38/16* (2013.01); *A61K 38/17* (2013.01); *A61K 45/06* (2013.01); *A61K 47/02* (2013.01);
(Continued)

(58) Field of Classification Search
None
See application file for complete search history.

(56) References Cited

U.S. PATENT DOCUMENTS

| | | |
|---|---|---|
| 3,940,480 A | 2/1976 | Suenaga et al. |
| 4,337,242 A | 6/1982 | Markus et al. |

(Continued)

FOREIGN PATENT DOCUMENTS

| | | |
|---|---|---|
| WO | WO 02-02793 | 1/2002 |
| WO | WO 2005-027821 | 3/2005 |

(Continued)

OTHER PUBLICATIONS

Alpha1-Proteinase Inhibitor (Human) Prolastin, Talecris Biotherapeutics, Inc. (2008).

(Continued)

*Primary Examiner* — Ernst V Arnold
*Assistant Examiner* — Kyung Sook Chang
(74) *Attorney, Agent, or Firm* — Womble Carlyle Sandridge & Rice, LLP

(57) ABSTRACT

The present invention provides compositions comprising API and at least one amino acid, in particular a liquid API formulation comprising amino acids, and methods and kits related thereto. These amino acids when incorporated into the API composition afford stability to the API formulation.

12 Claims, 27 Drawing Sheets

Related U.S. Application Data

(60) Provisional application No. 61/257,711, filed on Nov. 3, 2009.

(51) Int. Cl.
| | |
|---|---|
| *A61K 38/17* | (2006.01) |
| *A61K 38/16* | (2006.01) |
| *A61K 31/185* | (2006.01) |
| *A61K 45/06* | (2006.01) |
| *A61K 47/18* | (2017.01) |
| *A61K 9/00* | (2006.01) |
| *A61K 47/26* | (2006.01) |
| *A61K 47/20* | (2006.01) |
| *A61K 47/22* | (2006.01) |
| *A61K 47/02* | (2006.01) |

(52) U.S. Cl.
CPC .............. *A61K 47/20* (2013.01); *A61K 47/22* (2013.01); *A61K 47/26* (2013.01)

(56) References Cited

U.S. PATENT DOCUMENTS

| | | | |
|---|---|---|---|
| 4,340,589 A | 7/1982 | Uemura et al. | |
| 4,496,537 A | 1/1985 | Kwan | |
| 4,517,294 A | 5/1985 | Bock et al. | |
| 4,632,981 A | 12/1986 | Bock et al. | |
| 4,711,848 A | 12/1987 | Insley et al. | |
| 4,732,973 A | 3/1988 | Barr et al. | |
| 4,873,316 A | 10/1989 | Meade et al. | |
| 4,931,373 A | 6/1990 | Kawasaki et al. | |
| 5,032,405 A | 7/1991 | Huang et al. | |
| 5,079,336 A | 1/1992 | Rubin et al. | |
| 5,134,119 A | 7/1992 | Lezdey et al. | |
| 5,218,091 A | 6/1993 | Kawasaki et al. | |
| 5,304,638 A | 4/1994 | Marshall et al. | |
| 5,322,775 A | 6/1994 | Clark et al. | |
| 5,420,252 A | 5/1995 | Kato et al. | |
| 5,561,115 A | 10/1996 | Tenold et al. | |
| 5,618,713 A | 4/1997 | Zettlmeissl et al. | |
| 5,700,663 A | 12/1997 | Zettlmeissl et al. | |
| 5,843,705 A | 12/1998 | Ditullio et al. | |
| 6,072,029 A | 6/2000 | Courtney et al. | |
| 6,441,145 B1 | 8/2002 | Ditullio et al. | |
| 6,586,573 B1 | 7/2003 | Besman et al. | |
| 6,878,813 B2 | 4/2005 | Bock et al. | |
| 6,974,792 B2 | 12/2005 | Mattes et al. | |
| 7,019,193 B2 | 3/2006 | Ditullio et al. | |
| 7,087,723 B2 | 8/2006 | Besman et al. | |
| 7,247,707 B2 | 7/2007 | Besman et al. | |
| 7,777,006 B2 * | 8/2010 | Kee ..................... | B01D 15/327 435/7.1 |
| 2003/0235555 A1 | 12/2003 | Shealey et al. | |
| 2004/0157911 A1 | 8/2004 | Spireas et al. | |
| 2005/0013867 A1 | 1/2005 | Lehrman et al. | |
| 2005/0070477 A1 | 3/2005 | Cochrane | |
| 2005/0226893 A1 | 10/2005 | Juneau et al. | |
| 2006/0024793 A1 | 2/2006 | Yamada et al. | |
| 2007/0020199 A1 | 1/2007 | Platz et al. | |
| 2007/0105768 A1 * | 5/2007 | Nayar ..................... | A61K 9/19 435/212 |
| 2007/0237758 A1 | 10/2007 | Barry et al. | |
| 2008/0261868 A1 | 10/2008 | Shapiro | |
| 2008/0312136 A1 | 12/2008 | Durrani et al. | |

FOREIGN PATENT DOCUMENTS

| | | |
|---|---|---|
| WO | WO 2005-048985 | 6/2005 |
| WO | WO 2007-091267 | 8/2007 |
| WO | WO 2011-066291 | 6/2011 |

OTHER PUBLICATIONS

Antithrombin III (Human) Thrombate III, Talecris Biotherapeutics, Inc. (2006).
Arakawa, T., et al., "The Effects of Protein Stabilizers on Aggregation Induced by Multiple-Stresses," *Yakugaku Zasshi* 123(11): 957-961 (2003) (Abstract).
Archibald et al., "High-level expression of biologically active human a1-antitrypsin in the milk of transgenic mice," *PNAS*, 87:5178 (1990).
Coan, M.N., et al., "Preparation and Properties of Alpha,-Proteinase Inhibitor Concentrate from Human Plasma ," *Vox Sang.*, 48:333-342 (1985).
Fan, B., et al., "Heterogeneity of Recombinant Human Antithrombin III Expressed in Baby Hamster Kidney Cells," *JBC*, 268(23):17588-17596 (1993).
Garone, L., et al., "Antithrombin-Heparin Affinity Reduced by Fucosylation of Carbohydrate at Asparagine 155†," *Biochemistry*, 35:8881 (1996).
Gieseler, H., "Product Morphology and Drying Behavior delineated by a new Freeze-Drying Microbalance," *Thesis*, pp. 1-189 (2004).
Gillespie, L.S., et al., "Expression of Biologically Active Antithrombin III by Recombinant Baculovirus in *Spodoptera frugiperda Cella,*" *JBC*, 266:3995-4001 (1991).
Jennings, T.A., "Effect of formulation on lyophilization, part 1. Formulation components—their freezing and drying," *IVD Technology.* pp. 1-4 (1997).
Lu, X, and Pikal, M, "Freeze-drying of Mannitol-trehalose-sodium chloride-based formulations: the impact of annealing on dry layer resistance to Mass Transfer and Ckae Structure . Pharmaceutical Developmenet and Technology," 9(1):85-95 (2004).
Wright et al., "High-Level Expression of Active Human Alpha-1-Antitrypsin in the Mik of Transgenic Sheep," *Biotechnology*, 9:830-834 (1991).
Brochure of AralastTM manufactured by Alpha Therapeutic Corporation in which alpha 1-proteinase inhibitor is also known as alpha 1-antitrypsin (Dec. 2002).

\* cited by examiner

COMPOSITION, METHOD, AND KIT FOR ALPHA-1 PROTEINASE INHIBITOR

CROSS-REFERENCE TO RELATED APPLICATIONS

This application is a continuation of U.S. patent application Ser. No. 13/504,783, filed Jul. 20, 2012, which is a national phase of International Application No. PCT/US10/055135, filed Nov. 2, 2010, which claims priority under 35 USC §119 to U.S. Provisional Application No. 61/257,711, filed Nov. 3, 2009, each of which is herein incorporated by reference in its entirety.

FIELD OF THE INVENTION

The present invention relates to compositions comprising alpha 1-proteinase inhibitor (API), in particular stable API compositions. The present invention also relates to methods and kits for providing API to a subject, in particular for providing to the subject a therapeutically or prophylactically effective amount of API.

BACKGROUND OF THE INVENTION

API deficiency is a relatively common genetic disorder that predisposes affected individuals to liver disease and/or pulmonary emphysema. The most common type of API deficiency termed protease inhibitor type Z (PiZ), is transmitted as an autosomal recessive trait and affects approximately 1 in 1700 live births in most Northern European and North American populations. The PiZ mutation is a single nucleotide substitution that results in a single amino acid substitution (glutamate 342 to lysine).

Human API has 394 amino acids, one cysteine residue, and three carbohydrate side chains, giving an overall molecular weight of 52 kDa. A single reactive center loop (RCL) is located at a Met-Ser sequence at position 358-359. The tertiary structure of API contains 8 well-defined α-helices (A-H) and 3 large β-sheets (A-C). It is believed that serpins function via irreversible "suicide-substrate" mechanism. Upon cleavage by a protease, the serpin undergoes a conformational change, whereby the RCL is cleaved and inserted into the center of the A β-sheet, and the protease is translocated to the distal end of the molecule. This structural transition results in stabilization of the serpin and extensive distortion of the protease's tertiary structures, which inactivates its catalytic machinery. It is believed that the biological activity of API can be effected by, e.g., chemical modifications, including inter- or intramolecular polymerization, oxidation, complex formation, and/or cleavage by non-specific proteinases.

It is believed that the major physiological function of API is the inhibition of neutrophil elastase, cathepsin G, and proteinase 3. The API produced in individuals with PiZ API deficiency is functionally active, although there may be a decrease in its specific elastase inhibitory capacity. The predominant site of API synthesis is the liver, however, it is also synthesized in extrahepatic cell types including macrophages, intestinal epithelial cells and intestinal Paneth cells.

The pathogenesis of lung injury in API deficiency is attributable to the marked reduction in available API activity. API has been found to constitute greater than 90% of the neutrophil elastase inhibitor activity in pulmonary alveolar lavage fluid. Thus, it appears that the destructive lung disease seen in many individuals with API deficiency is due to a perturbation in the net balance between elastase and API within the lungs. The uninhibited activity of neutrophil elastase, cathepsin G, and proteinase 3, in turn, results in slow destruction of the connective tissue integrity of the lungs. This destruction of connective tissue leads to over distension and a reduction in the retractive force of the lungs which results in decreased expiratory airflow. Smoking exacerbates the problem by causing oxidative inactivation of what API is present.

At present, treatment options for individuals with pathologies associated with API deficiency are limited. Liver disease associated with API deficiency has been treated by orthotopic liver transplantation. Somatic gene therapy to replace the defective API gene has been discussed, but has yet to be successfully used.

There remains a need, therefore, for API compositions that are stable and that provide desirable API plasma bioavailability levels following administration to a subject.

SUMMARY OF THE INVENTION

There is now provided, in one aspect, a composition comprising: (a) an alpha 1-proteinase inhibitor (API); and (b) at least one amino acid.

In another aspect, the present invention provides methods for preparing the composition.

In other aspects, kits comprising the composition are provided.

DETAILED DESCRIPTION

Figure 1:
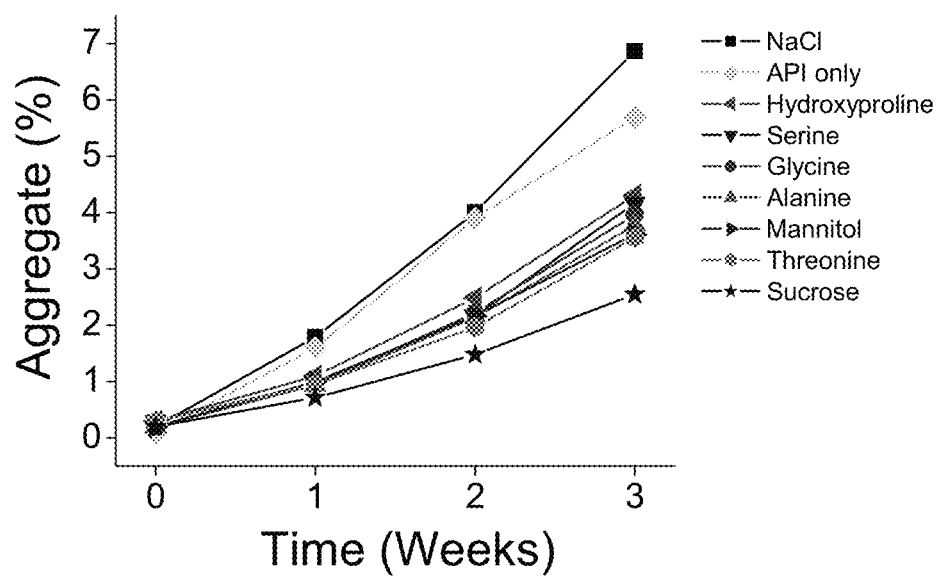
FIG. 1 is a graph showing the aggregation profiles of liquid API formulations shown in Table 1 of Example 1.

The present invention is based upon the discovery that a relatively stable API containing composition can be prepared by also including in the composition one or more amino acids. In particular embodiments, the present invention encompasses a stable API containing pharmaceutical composition suitable for providing API for administration to a subject for therapeutic or prophylactic effects. Non-limiting examples of disorders and diseases associated with API (e.g., lower than normal plasma API levels) and for which the present embodiments can be especially useful include, without limitation, lung disease such as chronic obstructive pulmonary disease (COPD) (e.g., emphysema), liver disease, vascular disease (e.g., intracranial aneurysms, arterial fibromuscular dysplasia, severe bleeding disorders, and hypertension), panniculitis, eye disease (e.g., anterior uveitis), systemic necrotizing vasculitis, and Wegener's granulomatosis.

I. Composition

In one aspect, the present invention provides a composition comprising:
(i) API; and
(ii) at least one amino acid.

In some embodiments, the composition consists of or consists essentially of the API and at least one amino acid.

The composition of the present invention can be provided in a relatively pure form. For example, in some embodiments, the composition can be characterized as being of a pharmaceutical grade.

The composition can be in the form of a solid, a liquid, or a semi-solid. For example, the composition can be a liquid formulation including, but not limited to, an aqueous solution, aqueous suspension, oil suspension, etc. Alternatively, the composition can be a lyophilized preparation, dry powder, solid particles, etc. Other examples, without limitation, include colloidals, emulsions, gels, and ointments.

In one embodiment, the composition is a liquid formulation, preferably an aqueous solution. In another embodiment, the composition is suitable for pharmaceutical use, for example a pharmaceutical composition comprising a pharmaceutically acceptable carrier or diluent.

In one embodiment, the composition is a pharmaceutical composition comprising the API, the amino acid, and a pharmaceutically acceptable carrier. As used herein "pharmaceutically acceptable carrier" includes any and all solvents, dispersion media, coatings, and the like that are physiologically compatible. The type of carrier can be selected based upon the intended route of administration. In some embodiments, the carrier is suitable for administering by way of, but not limited to, intravenous, inhalation, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. Pharmaceutically acceptable carriers include sterile aqueous solutions or dispersions and sterile powders for the preparation of sterile injectable solutions or dispersion.

In some embodiments, the composition is sterile and stable under one or more conditions of manufacture and storage. The composition can be formulated as a solution, microemulsion, liposome, or other ordered structure. For example, sterile injectable solutions can be prepared by filtered sterilization. Dispersions can be prepared by incorporating the API into a sterile vehicle which contains a dispersion medium. In the case of sterile powders for the preparation of sterile injectable solutions, the preferred methods of preparation are vacuum drying and freeze-drying which provides a composition comprising a powder of the API and the amino acid plus any additional desired ingredient, preferably from a previously sterile-filtered solution thereof.

Exemplary diluents (e.g., for use for dilution, reconstitution, etc. of the composition) can include, but are not limited to, sterile water, bacteriostatic water for injection (BWFI), a pH buffered solution (e.g. phosphate-buffered saline), sterile saline solution, and Ringer's solution or dextrose solution. The diluent optionally contains a preservative. The amount of preservative employed is determined by assessing different preservative concentrations for compatibility with API and preservative efficacy testing.

Inhalation therapy involves the administration of a drug in an aerosol form to the respiratory tract. Aerosol delivery is based on the concept that delivery to the deep lung regions (alveoli), which account of 95% of lung epithelia, can significantly enhance the transport of the protein through the epithelial membrane if the molecule is bioavailable. The liquid aerosols can be generated by nebulizing solutions of the API. Alternatively, solid particles can be either in the form of a powder suspended in a propellant which is administered from a metered dose inhaler or simply as a powder that is administered from a dry powder inhaler. For example, solid particle aerosols can be prepared by lyophilizing (e.g., freeze-drying) the API from solution and then milling or grinding the lyophilized drug to the desired particle size distribution for pulmonary administration. Another technique involves spray drying, which is a dehydration process that utilizes heat from a hot gas stream (usually air) to evaporate dispersed droplets created by atomization of a continuous liquid feed. Using these methods, the composition comprising API can be dried into fine particles, preferably with suitable types and amounts of excipients such as that can act as water-replacing agents.

Pressurized metered dose inhalers are now well known in the art. Any pressurized metered dose inhaler that is suitable for application of drugs to the lungs or nose of a patient can be used. The aerosol formulation and metering valve can be selected to provide a therapeutically or prophylactically effective amount of the API.

A. API

The term "API," as used herein, is intended to be broad unless specifically stated otherwise. The term refers to all naturally occurring polymorphs of API. The term also includes functional fragments of API, chimeric proteins comprising API or functional fragments thereof, homologs obtained by analogous substitution of one or more amino acids of API, and species homologs. The term also refers to all API polypeptides that are a product of recombinant DNA technology including an API that is a product of transgenic technology. For example, the gene coding for API can be inserted into a mammalian gene encoding a milk whey protein in such a way that the DNA sequence is expressed in the mammary gland as described in, e.g., U.S. Pat. No. 5,322,775, which is herein incorporated by reference for its teaching of a method of producing a proteinaceous compound. The term also refers to all API proteins synthesized chemically by methods known in the art such as, e.g., solid-phase peptide synthesis. The term also refers to API prepared from plasma. The term also refers to API that can be obtained commercially. The API can correspond to a human or a non-human API.

In one embodiment, the API is plasma-derived API. In another embodiment, the API is prepared from Cohn Fraction IV-1 paste. In other embodiments, the API is prepared from an albumin-depleted plasma fraction, a Cohn V precipitate, or a pre-purified API preparation fraction. U.S. Pat. No. 6,974,792 is herein incorporated by reference for its teaching of a method of preparing API.

In other embodiments, the API is recombinant API. Amino acid and nucleotide sequences for API and/or production of recombinant API are described by, e.g., U.S. Pat. Nos. 4,711,848; 4,732,973; 4,931,373; 5,079,336; 5,134,119; 5,218,091; 6,072,029; and Wright et al., Biotechnology, 9:830 (1991); and Archibald et al., PNAS, 87:5178 (1990), each of which is herein incorporated by reference for its teaching of API sequences, recombinant API, and/or recombinant expression of API.

In one embodiment, the composition is characterized as comprising an API having a greater than 90% purity. In other embodiments, the API has a purity greater than 95%, preferably at least about 99%. In some embodiments, at least about 50%, illustratively, about 50% to about 100%, about 60% to about 90%, about 70% to about 80% of all API in the composition is active API.

In one embodiment, the composition comprises a therapeutically effective amount of API. A "therapeutically effective amount" refers to an amount effective, at dosages and for periods of time necessary, to achieve the desired therapeutic result, such as, for example, reduction or inhibition of emphysema associated with congenital deficiency of API. A therapeutically effective amount of API can vary according to factors such as the disease state, age, sex, and weight of the individual subject, and the ability of the API to elicit a desired response in the subject. A therapeutically effective amount also can be one in which any toxic or detrimental effects of API are outweighed by the therapeutically beneficial effects.

In other embodiments, the composition comprises a prophylactically effective amount of API. A "prophylactically effective amount" refers to an amount effective, at dosages and for periods of time necessary, to achieve the desired prophylactic result, such as, for example, preventing or inhibiting emphysema associated with congenital deficiency of API. A prophylactically effective amount can be determined as described above for the therapeutically effective amount.

One factor that may be considered when determining a therapeutically or prophylactically effective amount of API is the concentration of functionally active API expressed in a biological compartment of the subject receiving the treatment, such as, for example, in the lower respiratory tract or the epithelial lining fluid (ELF) of the subject. Another factor that also may be considered when determining a therapeutically or prophylactically effective amount of API is the pharmacology (e.g., pharmacokinetics) of the API.

The pharmacokinetics of API refers to the concentration or levels of API in the subject's blood. Pharmacokinetic parameters or measures of API levels in the blood include the area under the curve (AUC), $C_{min}$ (i.e., trough), and $C_{max}$. The AUC is the total exposure of API in the subject's blood over a fixed dosing period (e.g., 8, 12, and 24 hours). The $C_{min}$ (i.e., trough level) is the lowest blood level of API during a fixed dosing period. The $C_{max}$ is the highest or peak level achieved by API in the subject's blood over a fixed dosing period.

In one embodiment, the therapeutically or prophylactically effective amount that is administered is sufficient to achieve or maintain an API blood (e.g., plasma) trough level above a target threshold level. In one embodiment, the target threshold level is at least about 10 mg/dL, illustratively, about 10, 15, 20, 25, 30, 35, 40, 45, 50, 55, 60, 65, 70, 75, 80, 85, 90, 100, 110, 120, 130, 140, 150, 160, 170, 180, 190, and 200 mg/dL.

In another embodiment, the therapeutically or prophylactically effective amount is sufficient to achieve or maintain an API blood trough level of at least about 50 mg/dL. In other embodiments, the therapeutically or prophylactically effective amount of API is sufficient to maintain a blood API trough level of at least about 80 mg/dL.

In one embodiment, the concentration of API in the composition is at least about 0.1 mg/ml, illustratively, at least about: 0.1, 1, 5, 10, 20, 30, 40, 50, 60, 70, 80, 90, 100, and 1000 mg/ml. In one embodiment, the specific activity of API in the composition is at least about 0.05 mg active API per mg total protein, illustratively, at least about 0.05, 0.1, 0.2 mg, 0.3 mg, 0.4 mg, 0.5 mg, 0.6 mg, 0.7 mg, or more active API per mg total protein.

In some embodiments, the concentration of the API contained in the composition is, on a weight percentage basis (w/v), at least about 1%, illustratively, about 1 to about 60%, about 5 to about 55%, about 10 to about 45%, about 20 to about 30% (w/v).

B. Amino Acid

It is to be understood that the amino acids specifically recited herein are for illustrative purposes only and are not intended to be limiting the amino acids that can be used in accordance with the present invention. Other amino acids not specifically recited herein can be readily categorized based on their observed physical and chemical properties. Further, some of the amino acids recited herein have been exemplified in terms of the genetically encoded amino acids, however, the amino acid need not be restricted to the genetically encoded amino acids but also can include genetically non-encoded amino acids. For example, the amino acid also can include naturally occurring non-encoded amino acids and synthetic amino acids (e.g., β-alanine, hydroxyproline). Also contemplated are L-enantiomeric amino acids (L-amino acids) and D-amino acids as well as free amino acid forms and/or physiologically acceptable salt forms and/or mixtures thereof.

Table 1 lists some non-limiting examples of amino acids.

TABLE 1

Amino Acids.

| Amino Acid | Three Letter Code | Single Letter Code |
|---|---|---|
| glycine | Gly | G |
| alanine | Ala | A |
| valine | Val | V |
| leucine | Leu | L |
| isoleucine | Ile | I |
| methionine | Met | M |
| phenylalanine | Phe | F |
| tryptophan | Trp | W |
| proline | Pro | P |
| serine | Ser | S |
| threonine | Thr | T |
| cysteine | Cys | C |
| tyrosine | Tyr | Y |
| asparagine | Asn | N |
| glutamine | Gln | Q |
| lysine | Lys | K |
| arginine | Arg | R |
| histidine | His | H |
| aspartic acid | Asp | D |
| glutamic acid | Glu | E |

In one embodiment, the composition comprises at least one amino acid each selected from the group consisting of: Ala (A), Thr (T), hydroxyproline, Gly (G), Ser (S), Gln (Q), Phe (F), Trp (W), Met (M), acetyl cysteine, Leu (L), Ile (I), Val (V), Lys (K), Pro (P), Tyr (Y), His (H), Glu (E), Asn (N), Asp (D), and Arg (R).

In another embodiment, the at least one amino acid each is selected from the group consisting of: Ala (A), Thr (T), hydroxyproline, Gly (G), and Ser (S).

In other embodiments, the at least one amino acid is Ala (A) or Gly (G).

In some embodiments, the amino acid is a neutral amino acid or a hydrophilic amino acid. In another embodiment, a hydrophilic amino acid is an amino acid that is characterized as exhibiting a hydrophobicity of less than zero according to a consensus hydrophobicity scale.

In one embodiment, the at least one amino acid is present in the composition in a total amino acid amount that is sufficient to provide a stable API composition, for example as determined relative to an API composition not having the at least one amino acid.

In another embodiment, the total amino acid amount is an amount sufficient such that the API retains at least about 5% of an API activity for a period of time at a temperature, illustratively, at least about 5% to about 100%, about 10% to about 95%, about 20% to about 90%, about 30% to about 80%, about 40% to about 70%, and about 50% to about 60% of an API activity for a period of time at a temperature. In some embodiments, the period of time and/or the temperature is characterized as a storage time and/or temperature (e.g., shelf-life). In one embodiment, the period of time is at least about: 1 day, 1 week, 2 weeks, 3 weeks, 1 month, 2 months, 3 months, 4 months, 5 months, 6 months, 8 months, 1 year, 2 years, and 3 years. In another embodiment, the temperature is equal to or greater than about: −120° C., −70° C., −20° C., 0° C., 5° C., 25° C., 37° C., 40° C., and 50° C.

In one embodiment, the API activity can be determined by inhibition of porcine pancreatic elastase as described by, e.g., Coan et al., Vox Sang., 48:333 (1985), which is herein incorporated by reference in its entirety. In some embodiments, the API activity can be assessed as potency or as toxicity by an in vitro, in vivo, and/or ex vivo determination (e.g. therapeutic index, $LD_{50}$, $ED_{50}$, etc.) in an animal. For example, following serial dilutions from a bulk or stock solution, or reconstitution of a lyophilized, or vacuum dried API containing composition, the API present in the reconstituted or aqueous composition has (in the presence of the at least one amino acid and/or the total at least one amino acid amount) greater than at least about 5% to about 100% of the potency or toxicity that the biologically active API had prior to being incorporated into the composition.

In other embodiments, stability of the API can be determined by, for example, determining degradation of the API including, but not limited to, formation of oxidation, proteolytic, and/or deamidation products, changes in molecular weight distribution, changes in potency, changes in functionality, increases in insoluble matter such as aggregates or modification of the product due to the presence of excipients, such as non-enzymatic glycation. In addition, stability can be determined as a change in concentration due to, for example, volatilization, adsorption, chemical modification, and the like. Accordingly, in some embodiments, storage stable API compositions are those compositions that show less than 5, 10, 15, 20, 25, 30, 40, 50, 60, 70% API degradation. Storage stable compositions also can show any combination of these characteristics.

In another embodiment, the total amino acid amount of the composition is an amount sufficient to increase a melting point of API relative to a composition without the at least one amino acid. One of ordinary skill in the art can determine the melting point, for example using a differential scanning calorimeter (DSC). In one embodiment, the total amino acid amount of the composition is sufficient to raise the melting point by at least about: 0.01° C., 0.1° C., 1° C., 1.2° C., 1.4° C., 1.6° C., 1.8° C., and 2° C.

In other embodiments, the total amino acid amount of the composition, after storage of the composition at a period of time at a temperature, is an amount sufficient such that the percentage of monomeric API in the composition is at least about 50%, illustratively, about 50% to about 100%, about 60% to about 99%, about 98%, about 70% to about 98%, about 80% to about 95%, and about 85% to about 90%. In one embodiment, the period of time is at least about: 1 day, 1 week, 2 weeks, 3 weeks, 4 weeks, 5 weeks, 2 months, 3 months, 4 months, 5 months, 6 months, 8 months, 1 year, 2 years, and 3 years. In another embodiment, the temperature is equal to or greater than about: −120° C., −70° C., −20° C., 0° C., 5° C., 25° C., 37° C., 40° C., and 50° C.

In another embodiment, the total amino acid amount of the composition is an amount sufficient such that, after storage of the composition for a period of time at a temperature, the percentage of protein aggregates in the composition is less than or equal to about: 50%, 40%, 30%, 20%, 10%, 9%, 8%, 7%, 6%, 5%, 4%, 3%, 2%, 1%, 0.5%, and 0%. In one embodiment, the period of time is at least about: 1 day, 1 week, 2 weeks, 3 weeks, 4 weeks, 5 weeks, 2 months, 3 months, 4 months, 5 months, 6 months, 8 months, 1 year, 2 years, and 3 years. In another embodiment, the temperature is equal to or greater than about: −120° C., −70° C., −20° C., 0° C., 5° C., 25° C., 37° C., 40° C., and 50° C.

Protein aggregation levels in a composition can be determined by one of ordinary skill in the art, for example by using size-exclusion high-performance liquid chromatography (SE-HPLC).

In one embodiment, the total amino acid amount that is present in the composition is at least about 0.01 M, illustratively, about 0.01 to about 3 M, about 0.03 to about 1 M, about 0.05 to about 0.5 M, and about 0.1 to about 0.3 M.

In another embodiment, the total amino acid amount that is present in the composition is at least about 0.01 M, at least about 0.03, or at least about 0.3 M.

In other embodiments, the composition comprises alanine at a total alanine concentration of at least about 0.01 M alanine, illustratively, about 0.01 to about 1 M and about 0.01 to about 0.75 M alanine. In some embodiments, the at least one amino acid is alanine, wherein the composition does not contain an amino acid other than the alanine.

In one embodiment, the composition comprises threonine at a total threonine concentration of at least about 0.01 M threonine, illustratively, about 0.01 to about 1 M and about 0.1 to about 0.3 M threonine. In some embodiments, the at least one amino acid is threonine, wherein the composition does not contain an amino acid other than the threonine.

In another embodiment, the composition comprises hydroxyproline at a total hydroxyproline concentration of at least about 0.01 M hydroxyproline, illustratively, about 0.01 to about 1 M and about 0.1 to about 0.3 M hydroxyproline. In some embodiments, the at least one amino acid is hydroxyproline, wherein the composition does not contain an amino acid other than the hydroxyproline.

In one embodiment, the composition comprises glycine at a total glycine concentration of at least about 0.01 M glycine, illustratively, about 0.01 to about 1 M and about 0.1 to about 0.3 M glycine. In some embodiments, the at least one amino acid is glycine, wherein the composition does not contain an amino acid other than the glycine.

In other embodiments, the composition comprises serine at a total serine concentration of at least about 0.01 M serine, illustratively, about 0.01 to about 1 M and about 0.1 to about 0.3 M serine. In some embodiments, the at least one amino acid is serine, wherein the composition does not contain an amino acid other than the serine.

In one embodiment, the composition comprises glutamine at a total glutamine concentration of at least about 0.01 M glutamine, illustratively, about 0.01 to about 1 M and about 0.1 to about 0.3 M glutamine. In some embodiments, the at least one amino acid is glutamine, wherein the composition does not contain an amino acid other than the glutamine.

In other embodiments, the composition comprises phenylalanine at a total phenylalanine concentration of at least about 0.01 M phenylalanine, illustratively, about 0.01 to about 1 M and about 0.1 to about 0.3 M phenylalanine. In some embodiments, the at least one amino acid is phenylalanine, wherein the composition does not contain an amino acid other than the phenylalanine.

In one embodiment, the composition comprises tryptophan at a total tryptophan concentration of at least about 0.01 M tryptophan, illustratively, about 0.01 to about 1 M and about 0.1 to about 0.3 M tryptophan. In some embodiments, the at least one amino acid is tryptophan, wherein the composition does not contain an amino acid other than the tryptophan.

In another embodiment, the composition comprises methionine at a total methionine concentration of at least about 0.01 M methionine, illustratively, about 0.01 to about 1 M and about 0.1 to about 0.3 M methionine. In some embodiments, the at least one amino acid is methionine, wherein the composition does not contain an amino acid other than the methionine.

In other embodiments, the composition comprises acetyl cysteine at a total acetyl cysteine concentration of at least about 0.01 M acetyl cysteine, illustratively, about 0.01 to about 1 M and about 0.1 to about 0.3 M acetyl cysteine. In some embodiments, the at least one amino acid is acetyl cysteine, wherein the composition does not contain an amino acid other than the acetyl cysteine.

In one embodiment, the composition comprises leucine at a total leucine concentration of at least about 0.01 M leucine, illustratively, about 0.01 to about 1 M and about 0.03 to about 0.15 M leucine. In some embodiments, the at least one amino acid is leucine, wherein the composition does not contain an amino acid other than the leucine.

In another embodiment, the composition comprises isoleucine at a total isoleucine concentration of at least about 0.01 M isoleucine, illustratively, about 0.01 to about 1 M and about 0.1 to about 0.3 M isoleucine. In some embodiments, the at least one amino acid is isoleucine, wherein the composition does not contain an amino acid other than the isoleucine.

In other embodiments, the composition comprises valine at a total valine concentration of at least about 0.01 M valine, illustratively, about 0.01 to about 1 M and about 0.1 to about 0.3 M valine. In some embodiments, the at least one amino acid is valine, wherein the composition does not contain an amino acid other than the valine.

In one embodiment, the composition comprises lysine at a total lysine concentration of at least about 0.01 M lysine, illustratively, about 0.01 to about 1 M and about 0.1 to about 0.3 M lysine. In some embodiments, the at least one amino acid is lysine, wherein the composition does not contain an amino acid other than the lysine.

In another embodiment, the composition comprises proline at a total proline concentration of at least about 0.01 M proline, illustratively, about 0.01 to about 1 M and about 0.1 to about 0.3 M proline. In some embodiments, the at least one amino acid is proline, wherein the composition does not contain an amino acid other than the proline.

In other embodiments, the composition comprises tyrosine at a total tyrosine concentration of at least about 0.01 M tyrosine, illustratively, about 0.01 to about 1 M and about 0.1 to about 0.3 M tyrosine. In some embodiments, the at least one amino acid is tyrosine, wherein the composition does not contain an amino acid other than the tyrosine.

In one embodiment, the composition comprises histidine at a total histidine concentration of at least about 0.01 M histidine, illustratively, about 0.01 to about 1 M and about 0.1 to about 0.3 M histidine. In some embodiments, the at least one amino acid is histidine, wherein the composition does not contain an amino acid other than the histidine.

In another embodiment, the composition comprises glutamic acid at a total glutamic acid concentration of at least about 0.01 M glutamic acid, illustratively, about 0.01 to about 1 M and about 0.1 to about 0.3 M glutamic acid. In some embodiments, the at least one amino acid is glutamic acid, wherein the composition does not contain an amino acid other than the glutamic acid.

In other embodiments, the composition comprises asparagine at a total asparagine concentration of at least about 0.01 M asparagine, illustratively, about 0.01 to about 1 M and about 0.1 to about 0.3 M asparagine. In some embodiments, the at least one amino acid is asparagine, wherein the composition does not contain an amino acid other than the asparagine.

In one embodiment, the composition comprises aspartic acid at a total aspartic acid concentration of at least about 0.01 M aspartic acid, illustratively, about 0.01 to about 1 M and about 0.1 to about 0.3 M aspartic acid. In some embodiments, the at least one amino acid is aspartic acid, wherein the composition does not contain an amino acid other than the aspartic acid.

In another embodiment, the composition comprises arginine at a total arginine concentration of at least about 0.01 M arginine, illustratively, about 0.01 to about 1 M and about 0.17 to about 0.3 M arginine. In some embodiments, the at least one amino acid is arginine, wherein the composition does not contain an amino acid other than the arginine.

C. Excipients

In other embodiments, the present invention provides a composition comprising:

(i) an API;

(ii) at least one amino acid, wherein the composition further comprises one or more excipients. Non-limiting examples of excipients include polyols, sugars, surfactants, antioxidants, salts (e.g., inorganic salts), metal chelators, polymers (e.g., polyethylene glycol (PEG), cyclodextrin, dextran), urea, guanidium chloride, polypeptides (e.g., antibodies), and combinations thereof. Accordingly, one of skill in the art will understand that the term "excipients" as used herein is intended to be broad and can include such agents as commonly used by one of ordinary skill in the art to prepare protein containing compositions.

In some embodiments, the excipient is a polyol or a sugar. For example, the polyol or sugar can be, but is not limited to, sucrose, mannitol, trehalose, sorbitol, sorbose, melezitose, glycerol, fructose, mannose, maltose, lactose, arabinose, xylose, ribose, rhamnose, galactose, glucose, xylitol, erythritol, threitol, raffinose, and/or the like.

In one embodiment, the one or more excipients each is selected from the group consisting of: sucrose, mannitol, glycerol, sorbitol, dextran, trehalose, hydroxyethyl starch (HES), saccharin sodium, polyethylene glycol (PEG) (e.g., PEG 3350, PEG 2000, PEG 8000), and 1,2-propanediol. In another embodiment, the excipient is sucrose or mannitol.

In other embodiments, the total amount of sucrose, if present in the composition, is less than 20% (w/v), illustratively, about 0% to about 15% (w/v), about 2.5% to about 7.5%, and about 4% to about 5% (w/v). In one embodiment, the composition does not contain sucrose.

The total amount of each excipient and/or the total excipient amount of the composition can vary, for example depending on the type and/or amount of excipients used and/or the type and/or amount of other components present in the composition comprising the API.

In one embodiment, the composition comprises a sugar at a total sugar concentration of at least about 0.01 M sugar, illustratively, about 0.01 to about 1 M and about 0.125 to about 0.75 M sugar. In some embodiments, the sugar is sucrose. In other embodiments, the sugar is sucrose, wherein the composition does not contain a sugar other than the sucrose.

In another embodiment, the composition comprises a polyol at a total polyol concentration of at least about 0.01 M polyol, illustratively, about 0.01 to about 1 M and about 0.25 to about 0.75 M polyol. In some embodiments, the polyol is mannitol. In other embodiments, the polyol is mannitol, wherein the composition does not contain a polyol other than the mannitol.

In other embodiments, the composition comprises a polyol at a total polyol concentration of at least about 0.25% (w/v) polyol, illustratively, about 0.25 to about 5% (w/v) polyol. In some embodiments, the polyol is glycerol. In other embodiments, the polyol is glycerol, wherein the composition does not contain a polyol other than the glycerol.

In one embodiment, the composition comprises a polyol at a total polyol concentration of at least about 0.01 M polyol, illustratively, about 0.01 to about 1 M and about 0.27 to about 0.55 M polyol. In some embodiments, the polyol is sorbitol. In other embodiments, the polyol is sorbitol wherein the composition does not contain a polyol other than the sorbitol.

In another embodiment, the composition comprises a polymer at a total polymer concentration of at least about 0.25% (w/v) polymer, illustratively, about 0.25 to about 5% (w/v) polymer. In some embodiments, the polymer is dextran. In other embodiments, the polymer is dextran, wherein the composition does not contain a polymer other than the dextran.

In other embodiments, the composition comprises a sugar at a total sugar concentration of at least about 0.01 M sugar, illustratively, about 0.01 to about 1 M and about 0.15 to about 0.75 M sugar. In some embodiments, the sugar is trehalose. In other embodiments, the sugar is trehalose, wherein the composition does not contain a sugar other than the trehalose.

In one embodiment, the composition comprises HES at a total HES concentration of at least about 0.25% (w/v) HES, illustratively, about 0.25 to about 5% (w/v) HES.

In another embodiment, the composition comprises saccharin sodium at a total saccharin sodium concentration of at least about 0.01 M saccharin sodium, illustratively, about 0.01 to about 1 M and about 0.15 to about 0.75 M saccharin sodium.

In other embodiments, the composition comprises a PEG at a total PEG concentration of at least about 0.25% (w/v) PEG, illustratively, about 0.25 to about 10% (w/v) PEG, and about 1 to about 5% (w/v) PEG. In some embodiments, the PEG is PEG 3350. In other embodiments, the PEG is about 5% (w/v) PEG 3350, wherein the composition does not contain a PEG other than the PEG 3350.

In one embodiment, the composition comprises 1,2-propanediol at a total 1,2-propanediol concentration of at least about 0.01 M 1,2-propanediol, illustratively, about 0.01 to about 1 M and about 0.125 to about 0.3 M 1,2-propanediol.

Surfactants can include, without limitation, e.g., block polymers of polyethylene and polypropylene glycol (e.g., Pluronic F68); or polyethylene glycol sorbitan monolaurates (e.g., Tween 80), polyoxyethylenesorbitan monooleates (e.g., Tween 20), and/or the like. In one embodiment, the surfactant is Pluronic F68 or Tween 80 (i.e., Polysorbate 80).

In one embodiment, the composition further comprises a surfactant at a total surfactant concentration of at least about 0.0025% (v/v) surfactant, illustratively, about 0.0025 to about 1% (v/v) surfactant, about 0.025 to about 0.1% (v/v) surfactant, and about 0.05 to about 0.075% (v/v) surfactant. In some embodiments, the surfactant is Pluronic F68 or Tween 80.

In another embodiment, the present invention provides a composition comprising:
(i) an API;
(ii) at least one amino acid, wherein the composition further comprises a salt, preferably an inorganic salt. Without limitation, examples of inorganic salts include sodium chloride or sodium phosphate.

In one embodiment, the inorganic salt is present in the composition in a total inorganic salt amount of at least 0.01 M, illustratively, about 0.01 to about 0.5 M, about 0.05 to about 0.4 M, and about 0.1 to about 0.15 M inorganic salt. In some embodiments, the inorganic salt is sodium chloride, sodium phosphate, or a combination thereof.

As used herein, the term "antioxidant" refers to an agent that reduces or prevents oxidation. "Antioxidants" include, but are not limited to, methionine, glutathione, acetylcysteine, ascorbic acid, butyl hydroxyl anisol (BHA), butyl hydroxyl toluene (BHT), and maleic acid.

In one embodiment, the present invention provides a composition comprising:
(i) an API;
(ii) at least one amino acid, wherein the composition further comprises an antioxidant. In some embodiments, the antioxidant is methionine. In other embodiments, the antioxidant is glutathione. In another embodiment, the antioxidant is present in the composition in a total antioxidant amount of at least about 0.01% (w/v), illustratively, about 0.01 to about 5% (w/v), and about 0.05 to about 0.7% (w/v).

Non-limiting examples of a metal chelator include ethylenediaminetetraacetic acid (EDTA), (0.1-0.5%), [ethylenebis (oxyethylenenitrilo)] tetraacetic acid (EGTA), 1,2-bis (2-aminophenoxy)ethane-N,N,N',N'-tetraacetic acid (BAPTA), hydroxyethlene triamine diacetic acid (HEDTA), or salts thereof. In one embodiment, the metal chelator is a divalent metal chelator. In another embodiment, the metal chelator is EDTA, EGTA, BAPTA, HEDTA, or salts thereof. In some embodiments, the composition comprises a combination of metal chelators. In other embodiments, the metal chelator is present in the composition at a total chelator amount of at least about 0.01% (w/v), illustratively, about 0.01 to about 1% (w/v), about 0.05 to about 0.5% (w/v), and about 0.1 to about 0.25%.

In another embodiment, the present invention provides a composition comprising:
(i) an API;
(ii) at least one amino acid, wherein the composition further comprises a metal chelator.

Accordingly, in other embodiments, the present invention provides a composition comprising:
(a) API; and
(b) an amino acid,
wherein the composition further comprises, or optionally further comprises, one or more excipients.

A variety of different API containing compositions are provided in accordance with the present invention. The active ingredient within such formulations is API, which can be human or non-human recombinant API but, as indicated above, also may include API extracted from plasma sources. Although the API can be present by itself as the sole active ingredient, the API also may be present with one or more additional active ingredient.

II. Method for Preparing the Composition

In other aspects, the present invention provides a method for preparing a composition comprising API and at least one amino acid.

In one embodiment, the method comprises dialyzing a first composition comprising API to remove a salt, if present in the composition.

For example, the first composition can be an API containing composition prepared in or contacted with a buffer, wherein the first composition comprises the salt. The composition can be, but is not limited, to a composition obtained from a bulk manufacturing process for preparing API from plasma (e.g., human plasma) or recombinant API preparations.

In one embodiment, the first composition comprises API in a phosphate buffer (e.g., 20 mM sodium phosphate, pH 7), wherein sodium chloride is present in the buffer, e.g., at about 100 mM NaCl. In some embodiments, dialyzing is preformed using ultrafiltration/diafiltration (UF/DF).

In some embodiments, the method further comprises providing at least one amino acid to the composition following the step of dialyzing. Excipients and/or any other reagents, etc. may be added along with the amino acid, following amino acid addition, or subsequent to amino acid addition.

In other embodiments, the method comprises dialyzing a first composition comprising API against a buffer (e.g., a phosphate buffer 20 mM, pH 7) comprising the at least one amino acid and/or excipients and/or any other reagent.

In one embodiment, the method further comprises maintaining the pH of the API containing composition at about 6.0 to about 8.0, preferably about 6.6 to about 7.4. For example, in another embodiment, a buffer salt can be added first to achieve the effective pH range, followed by addition of amino acids and/or excipients and/or any other reagents/ingredients. In other embodiments, amino acids and/or excipients, and or other reagents can be combined for adding to the API containing composition.

III. Kit

In other aspects, the present invention further provides a kit, e.g., a kit for treating a disease or condition associated API expression or activity. In one embodiment, the kit comprises a composition in accordance with the present invention, in particular a pharmaceutical composition comprising an API and an amino acid; and, optionally, instruction for use in treating or preventing the disease or condition associated API, for example a disease or condition associated with or caused by lower than normal plasma API levels.

In other embodiments, separate containers are provided by the kit, wherein at least one container comprises the API containing composition, and, in one or more further containers, a different composition, in particular a composition comprising an active ingredient other than API. Optionally, the kit can contain still further pharmaceutically acceptable carriers and diluents in combination with the active ingredients, and/or, separate therefrom in a separate container.

The present invention will be illustrated in more detail by way of Examples, but it is to be noted that the invention is not limited to the Examples.

EXAMPLES

Example 1

Stability of Liquid Formulations Comprising API

An accelerated stability study was performed in order to determine the stability of liquid formulations comprising API.

API prepared from a fraction IV-1 manufacturing and macro bench lot was subjected to dialysis against phosphate buffers (20 mM, pH 7) to remove salt and then concentrated to 100 mg/ml. Following dialysis, various API formulations containing other ingredients were obtained by adding a 2-fold solution containing the other ingredient(s). The final API formulation was then tested for API stability by adding about 2 ml of the final formulation into a 10 ml tubing vial, which was then incubated in a temperature-controlled chamber at 40° C. for ~3-4 weeks. Samples were collected every week to determine aggregate levels using SEC-HPLC.

The result are shown in FIG. 1 and summarized in Table 2.

TABLE 2

Percent aggregate levels of API liquid formulations.

| Formulation (50 mg/ml API) | % Aggregation at 40° C. | | | |
|---|---|---|---|---|
| | Week 0 | Week 1 | Week 2 | Week 3 |
| API only | 0.1 | 1.6 | 3.9 | 5.7 |
| API + 0.1M NaCl | 0.2 | 1.8 | 4.0 | 6.9 |
| API + 0.3M Hydroxyproline | 0.3 | 1.1 | 2.5 | 4.3 |
| API + 0.3M Serine | 0.3 | 1.0 | 2.2 | 4.2 |
| API + 0.3M Glycine | 0.2 | 1 | 2.2 | 4.0 |
| API + 0.3M Alanine | 0.2 | 1 | 2.1 | 3.8 |
| API + 0.3M Mannitol | 0.2 | 1 | 2.2 | 3.6 |
| API + 0.3M Threonine | 0.3 | 1 | 2 | 3.6 |
| API + 0.3M Sucrose | 0.2 | 0.7 | 1.5 | 2.6 |

As shown in FIG. 1 and Table 2, the formulation containing API alone and the formulation containing 0.1 M NaCl exhibited the most amount of aggregation. The API formulation containing sucrose was the most stable with the least amount of aggregates forming over time.

The accelerated stability study also was conducted at 40° C. with liquid API formulations containing API (50 mg/mL); API (50 mg/mL) plus alanine (0.25M) or sucrose (0.25M); and API (50 mg/mL) plus alanine (0.125M)/sucrose (0.125M).

Figure 2:
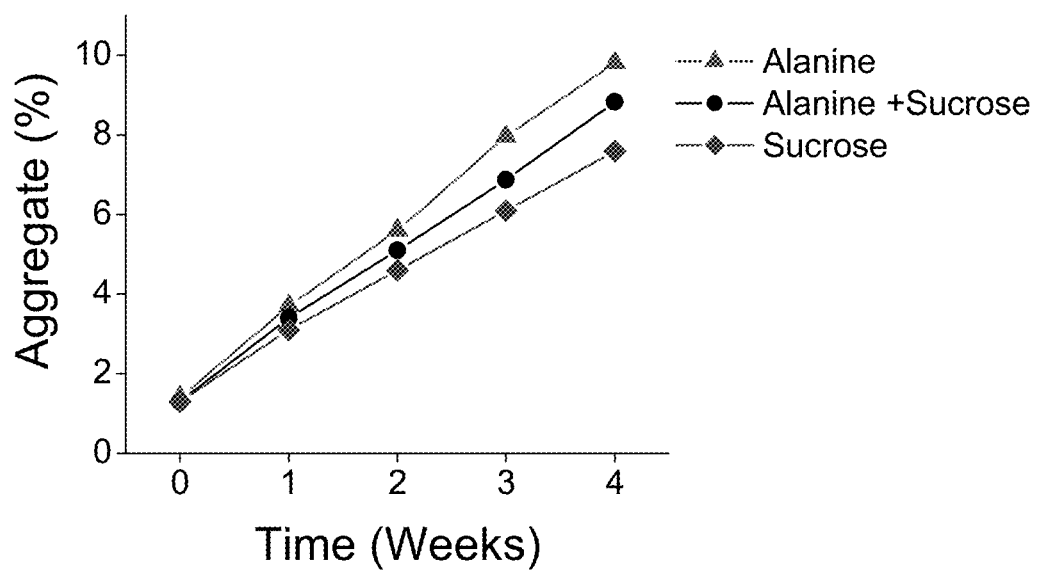
FIG. 2 is a graph showing the aggregation profiles of API formulations containing alanine, sucrose, or sucrose/alanine.

As shown in FIG. 2, alanine alone conferred a degree of stability to an API containing composition as determined by percent aggregate levels over time. Moreover, combining a limited amount of sucrose with alanine also provided a degree of stability, which was greater than alanine alone.

Example 2

Stability of Liquid Formulations Comprising API

The accelerated stability study described in Example 1 also was conducted at 40° C. with liquid API formulations containing API (50 mg/mL); API (50 mg/mL) plus alanine (0.25M) or mannitol (0.25M); and API (50 mg/mL) plus alanine (0.125M)/mannitol (0.125M).

Figure 3:
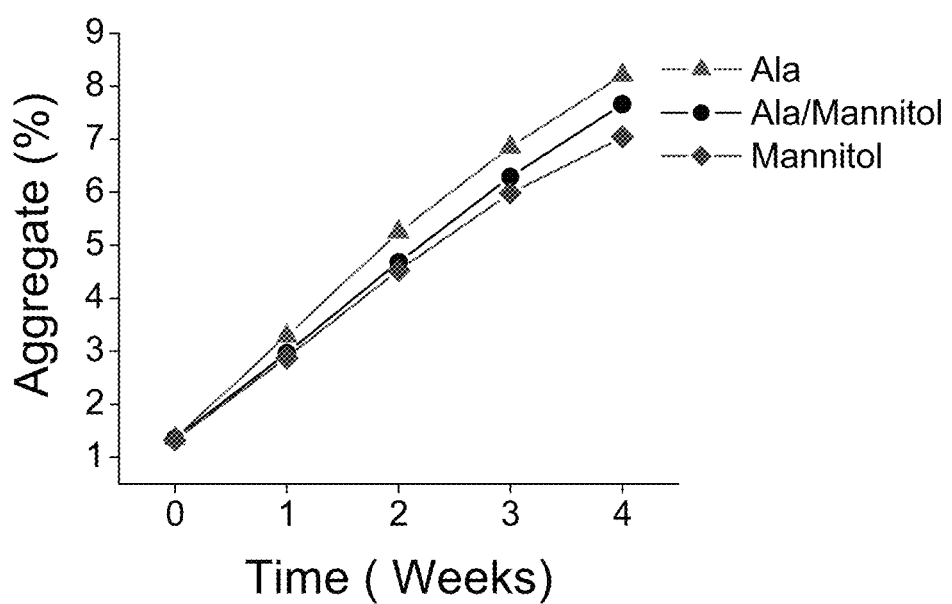
FIG. 3 is a graph showing the aggregation profiles of API formulations containing alanine, mannitol, or mannitol/alanine.

As shown in FIG. 3, alanine alone conferred a degree of stability to an API containing composition as determined by percent aggregate levels over time. Moreover, combining a limited amount of mannitol with alanine also provided a degree of stability, which was greater than alanine alone.

Example 3

Stability of Liquid Formulations Comprising API

The accelerated stability study described in Example 1 also was conducted at 40° C. to determine the stabilization effect of sucrose, trehalose, and alanine at various concentrations. In order to assess the stabilization effects of sucrose, trehalose and alanine, ten formulations containing these ingredients at 0.25 M, 0.5 M, and 0.75 M, respectively, were prepared and aseptically filled into 5 ml tubing vials. The aggregation of these samples at 40° C. was tested for 4 weeks.

Figure 4:
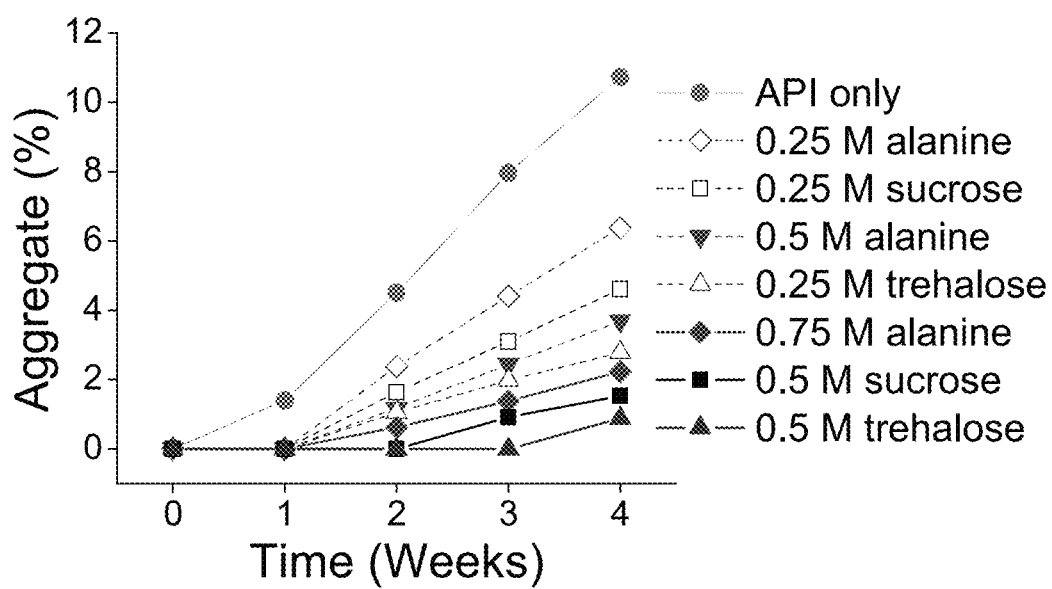
FIG. 4 is a graph showing the aggregation profiles of API formulations containing alanine, sucrose, or trehalose.

The results are shown in FIG. 4. The starting aggregate level was 0. During the 4 week incubation, no aggregation of API was detected in 0.75 M sucrose or 0.75 M trehalose formulations. No aggregation was detected at the first week at 40° C. API without the presence of the various ingredients aggregated at the first week and the aggregate level was highest at each time point. Aggregate level decreased with the increase in the concentration of the added ingredients. Trehalose provided the best stabilization effect against aggregation, followed by sucrose and alanine.

Example 4

Stability of Liquid Formulations Comprising API

The accelerated stability study described in Example 1 also was conducted at 40° C. to determine the effect of the concentration of alanine or glycine on API formulations. Alanine or glycine at 0 M, 0.1 M, 0.15 M, 0.2 M, 0.25 M, or 0.3 M were added to API liquid formulations and the aggregate levels compared at different time intervals at 40° C. All formulations started with about 1.3-1.4% aggregate levels.

Figure 5:
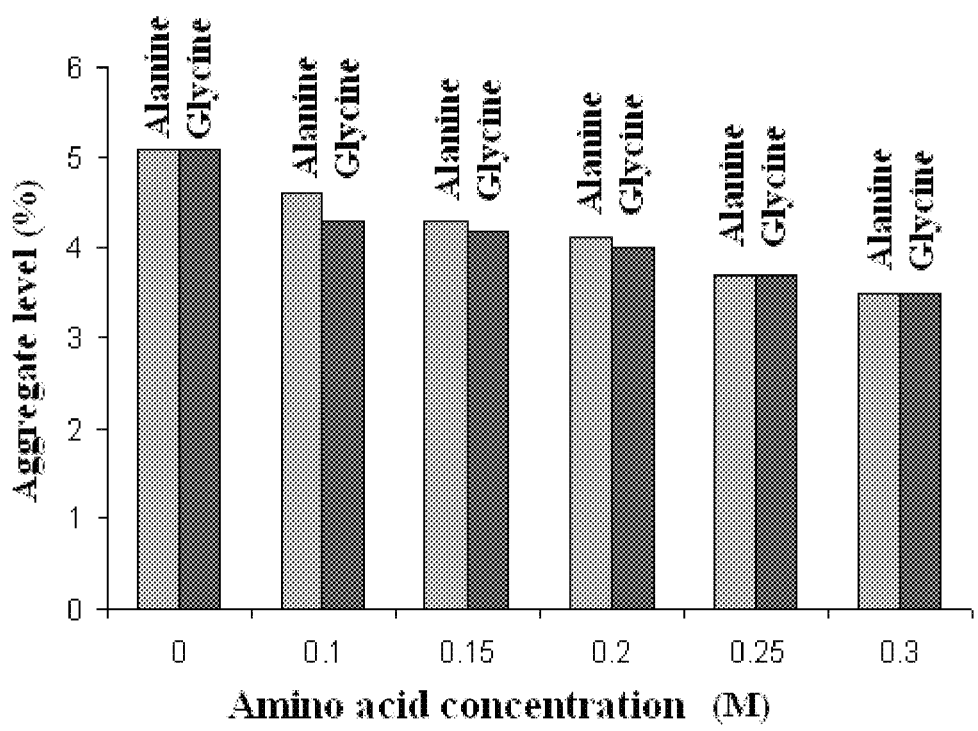
FIG. 5 is a graph showing the effect of amino acid concentration on aggregation of API formulations after incubating at 40° C. for one week.
Figure 6:
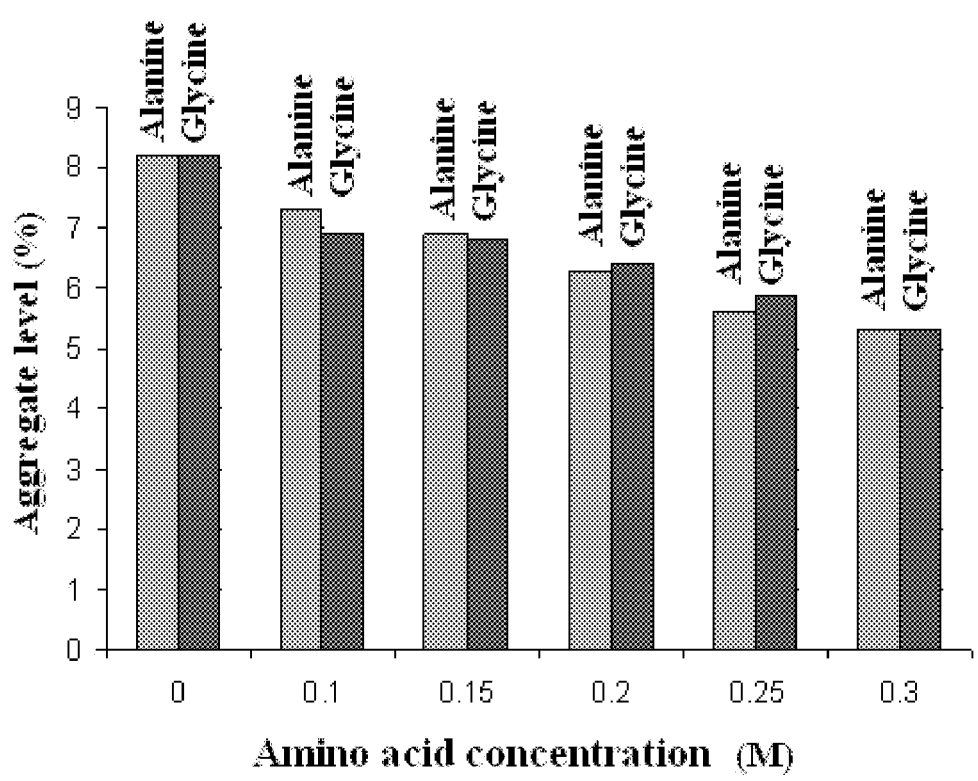
FIG. 6 is a graph showing the effect of amino acid concentration on aggregation of API formulations after incubating at 40° C. for two weeks.

FIG. 5 shows the aggregate levels in API liquid solutions formulated with different concentrations of alanine or glycine after incubating at 40° C. for 1 week. The aggregate level is reduced with the increase in the alanine or glycine concentration. FIG. 6 shows the aggregate levels at 2 weeks. The results agree with the 1 week data. The aggregate level is reduced with the increase in alanine or glycine concentration. Aggregation in 3 and 4 weeks also indicate that the aggregation is less with more alanine or glycine added (data not shown).

Example 5

Stability of Liquid Formulations Comprising API

The accelerated stability study described in Example 1 also was conducted at 40° C. to determine the effect of oxygen scavengers on aggregation. Thus, liquid formulations containing API (50 mg/ml) and alanine (0.25 M) were prepared that further contained 0.3%, 0.5%, and 0.7% methionine.

Figure 7:
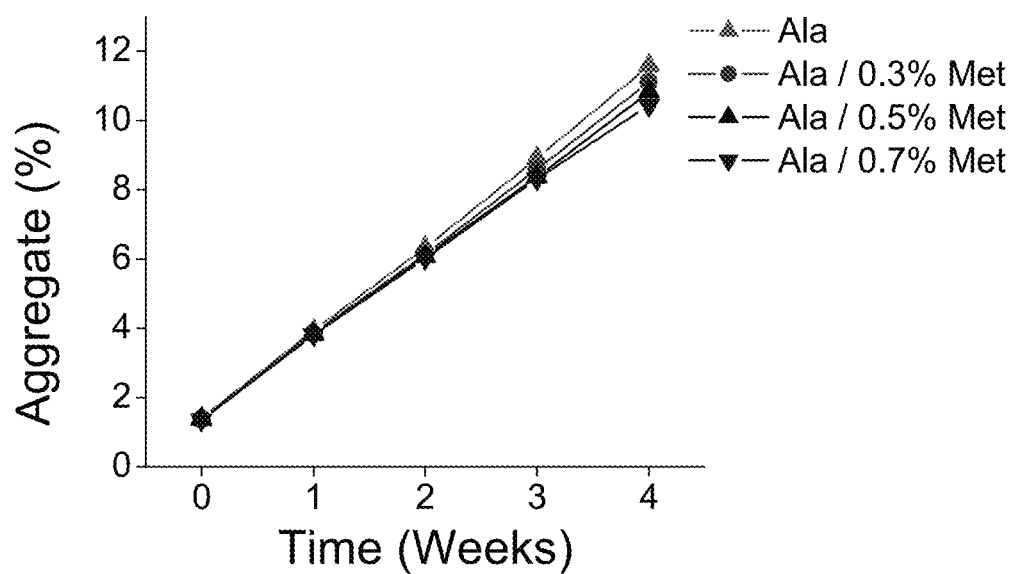
FIG. 7 is a graph showing the aggregation profiles of API formulations containing alanine with or without different concentrations of an oxygen scavenger.

FIG. 7 shows the aggregation profile at 40° C. The effect of methionine against aggregation is minimal. No significant reduction in aggregate level is observed.

Example 6

Stability of Liquid Formulations Comprising API

A bulk solution comprising alpha-1 proteinase inhibitor (API) (prepared from human plasma; 65 mg/ml potency) was obtained in 20 mM sodium phosphate buffer containing 100 mM sodium chloride. Ultrafiltration/diafiltration (UF/DF) was applied to dialyze the bulk solution (30 L) into phosphate buffer (20 mM, pH 7), using 240 L of phosphate buffer to reach the end point. Amino acids and/or other ingredients were added afterwards and the final protein concentration was adjusted to 50 mg/ml. The final formulation solution was filtered through a 0.22 μm filter and filled under a laminar flow hood. Filling volume was 20.0 ml. The vials were oversealed and labeled.

Formulation 1 contained 250 mM glycine; Formulation 2 contained 250 mM L-alanine; Formulation 3 contained 125 mM L-alanine and 4.2% sucrose; and Formulation 4 contained 100 mM sodium chloride. For each formulation, API was 50 mg/ml and the buffer was 20 mM sodium phosphate buffer (mixture of monobasic and dibasic heptahydrate). For a lyophilized product, additional assays including solubility time/visual appearance after reconstitution and cake moisture were performed.

Samples were placed on stability at 5° C. and 25° C. The following tests were conducted for initial (time 0) sample per formulation: appearance, fibrils, potency, pH, SEC-HPLC, measurement of light absorbance at $A_{280}$, Nephelometry (NTU) measurement, protein composition by capillary zone electrophoresis (CZE), deamidation and dynamic light scattering (DLS). Determination of sodium was performed by Atomic Absorption Spectrophotometry; determination of sucrose was performed by ion chromatography; nephelometry: turbidity determinations were performed using the HACH Ratio Turbidimeter; and quantitative determination of API was preformed using a 96-well plate based potency assay.

Table 3 shows the results from initial analytical testing.

TABLE 3

Results of initial analytical tests.

| Test | | 1 | 2 | 3 | 4 | Lyophilized |
|---|---|---|---|---|---|---|
| Appearance (Protein particles only) | | None | None | None | None | † |
| Appearance By CIE | L coord | 96.45 | 96.37 | 96.38 | 96.03 | 96.2 |
| | a coord | −0.61 | −0.6 | −0.56 | −0.76 | −0.72 |
| | b coord | 2.55 | 2.52 | 2.44 | 2.81 | 2.78 |
| NTU | | 2.89 | 2.83 | 2.62 | 4.77 | 4.71 |
| pH | | 6.97 | 7.00 | 7.03 | 6.92 | 7.01 |
| Alpha potency (mg/mL) | | 51.39 | 52.57 | 50.55 | 52.89 | 51.72 |
| $A_{280}$ AU | | 25.3 | 25.3 | 24.9 | 25.6 | 24.5 |
| Specific activity | | 2.03 | 2.08 | 2.03 | 2.07 | 2.11 |
| Alpha HPLC (% area) | Region 1 | 1.78 | 1.75 | 1.65 | 2.04 | 1.44 |
| | Region 2 | 6.45 | 6.43 | 6.43 | 6.42 | 6.51 |
| | Region 3 | 3.27 | 3.17 | 3.13 | 3.14 | 3.44 |
| | Region 4 | 0 | 0 | 0 | 0 | 0 |
| | Region 5 | 88.44 | 88.57 | 88.73 | 88.33 | 88.52 |
| | Fragment area | 0.07 | 0.09 | 0.07 | 0.08 | 0.11 |
| CZE (% area) | Gamma | 0 | 0 | 0 | 0 | 0 |
| | Beta | 0 | 0 | 0 | 0 | 0 |
| | Alpha 2 | 2.9 | 3.3 | 3.0 | 3.2 | 3.4 |
| | Alpha 1 | 97.1 | 96.7 | 97.1 | 96.8 | 96.7 |
| | Albumin | 0 | 0 | 0 | 0 | 0 |
| Sodium (mEq/L) | | 51.07 | 51.33 | 51.08 | 153.83 | 152.31 |
| Chloride (mEq/L) | | n/a | n/a | n/a | 96.0 | 88.0 |
| Phosphate (mEq/L) | | 1472.4 | 1472.3 | 1445.6 | 1511.7 | 1765.3 |
| Deamidation (% area) | | 5.9 | 6.4 | 6.4 | 6.7 | n/a |
| DLS | 1 Radius (nm) | 3.7 | 3.6 | n/a | 3.9 | n/a |
| | % Mass | 99.9 | 99.9 | n/a | 99.9 | n/a |

TABLE 3-continued

Results of initial analytical tests.

| Test | | Formulation | | | | |
| --- | --- | --- | --- | --- | --- | --- |
| | | 1 | 2 | 3 | 4 | Lyophilized |
| 2 | Radius (nm) | 23 | 25 | n/a | 25.1 | n/a |
| | % Mass | 0.1 | 0.1 | 0 | 0.1 | n/a |
| 3 | Radius (nm) | n/a | n/a | n/a | n/a | n/a |
| | % Mass | n/a | n/a | n/a | n/a | n/a |
| 4 | Radius (nm) | 188 | n/a | 365.3 | n/a | n/a |
| | % Mass | 0 | n/a | 0 | n/a | n/a |

† Off white cake, no protein particles, clear, 120 (pale yellow), solubilization time: 1 min.

Figure 8:
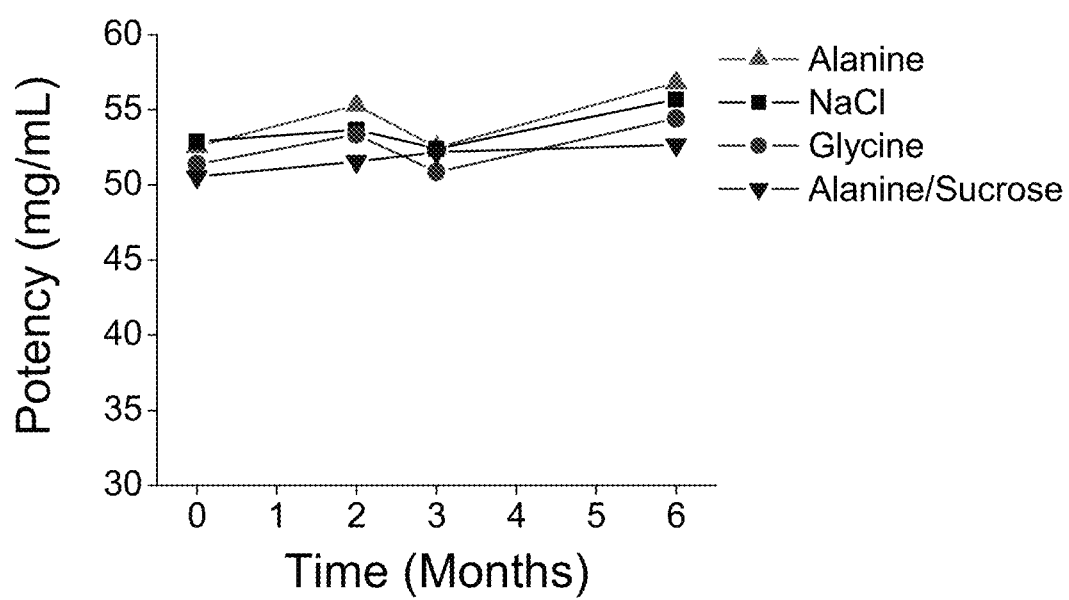
FIG. 8 is a graph showing potency profiles of API formulations described in Example 6 at 5° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 9:
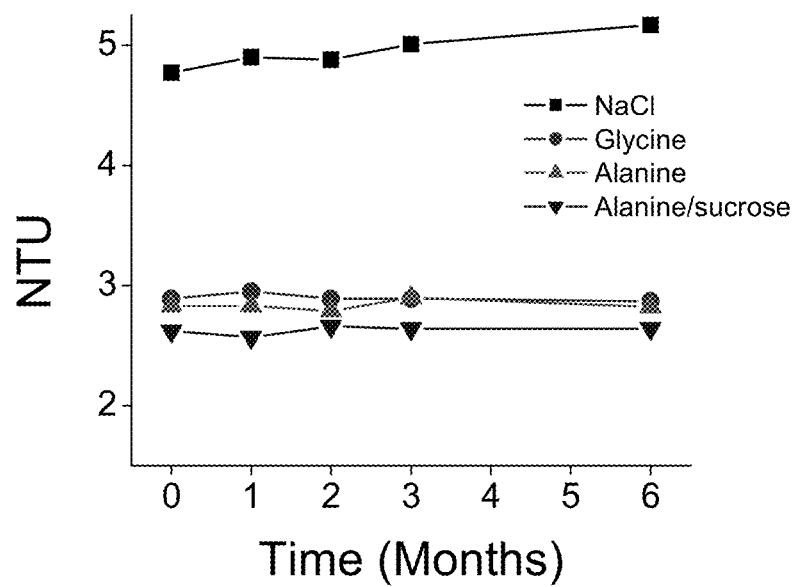
FIG. 9 is a graph showing nephelometry (NTU) profiles of API formulations described in Example 6 at 5° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 10:
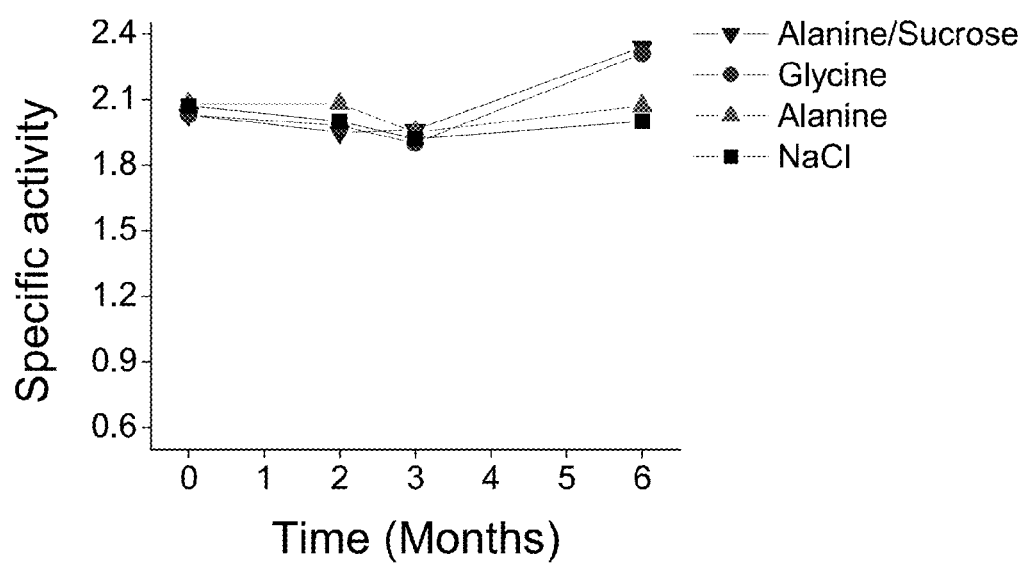
FIG. 10 is a graph showing specific activity profiles of API formulations described in Example 6 at 5° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 11:
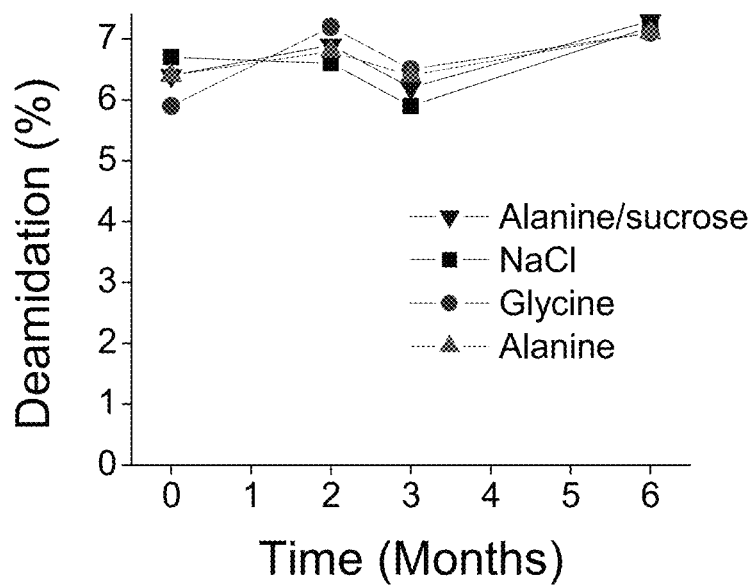
FIG. 11 is a graph showing deamidation profiles of API formulations described in Example 6 at 5° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).

5° C. stability data: At 5° C., few fibrils were observed in API formulated with alanine/sucrose (formulation 3) at 3 and 6 months. No fibril was noted in any other formulations for any time point. No significant change was observed in potency (FIG. 8), NTU (FIG. 9), pH, specific activity (FIG. 10), DLS and deamidation measurement (FIG. 11). The final container precision for potency (BCS) is 5%. The intermediate precision for NTU and deamidation are 3.0% and 18.5% respectively. The difference observed is within assay variability.

Size Exclusion chromatography (SEC-HPLC) separates the sample's protein based on the molecule's hydrodynamic volume. In SEC-HPLC, molecules with a large hydrodynamic volume have minimal (if any) interaction with the column's packing and elute off at the column's void volume ($V_0$). Molecules with a smaller hydrodynamic volume interact more with the column's packing and elute off the column after the void volume.

Figure 12:
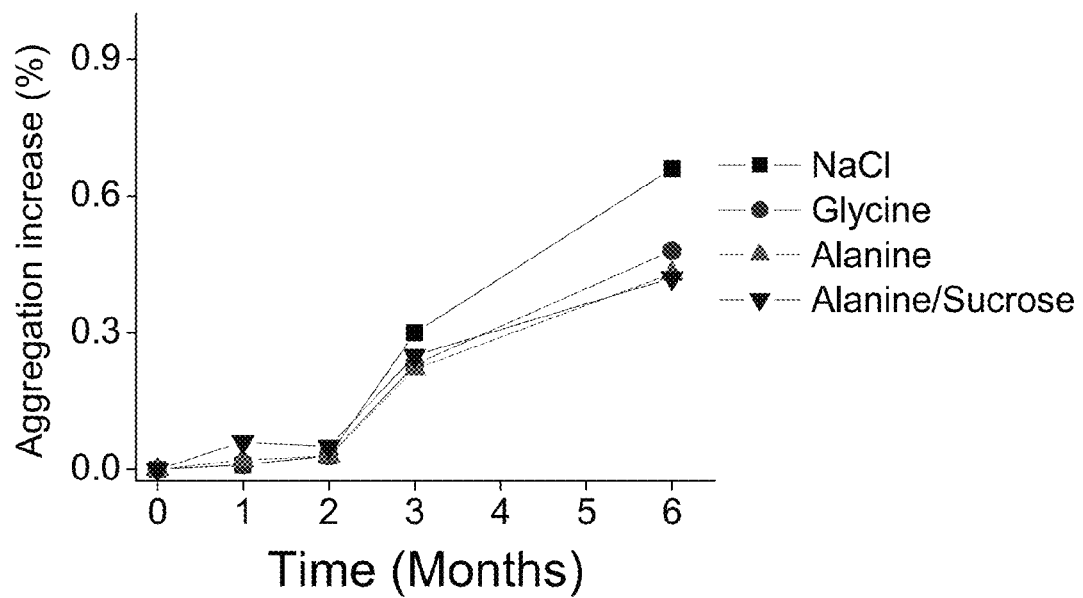
FIG. 12 is a graph showing aggregation increase profiles of API formulations described in Example 6 at 5° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 13:
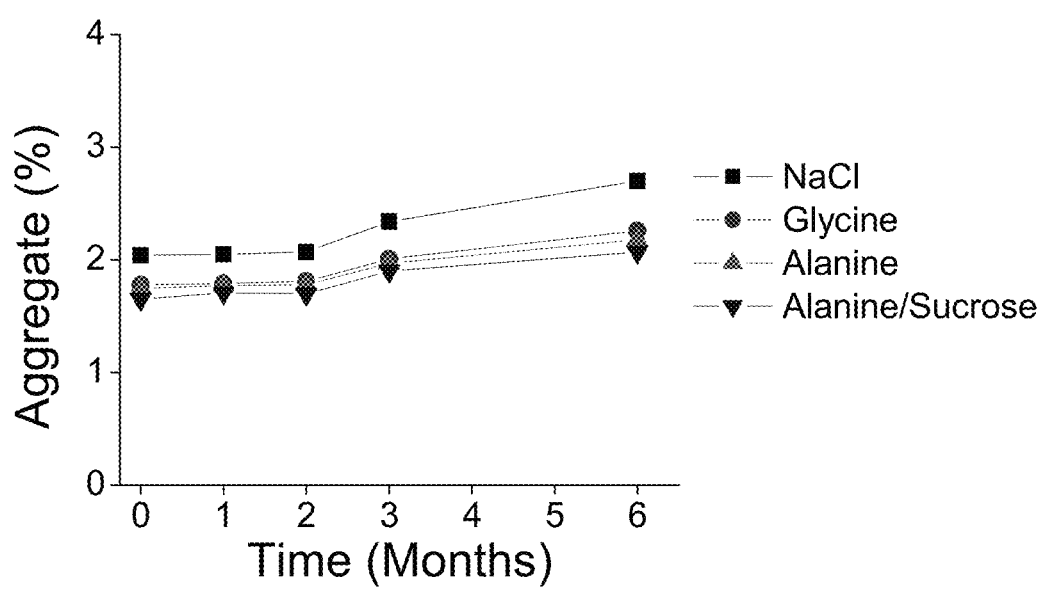
FIG. 13 is a graph showing aggregation profiles of API formulations as described in Example 6 at 5° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 14:
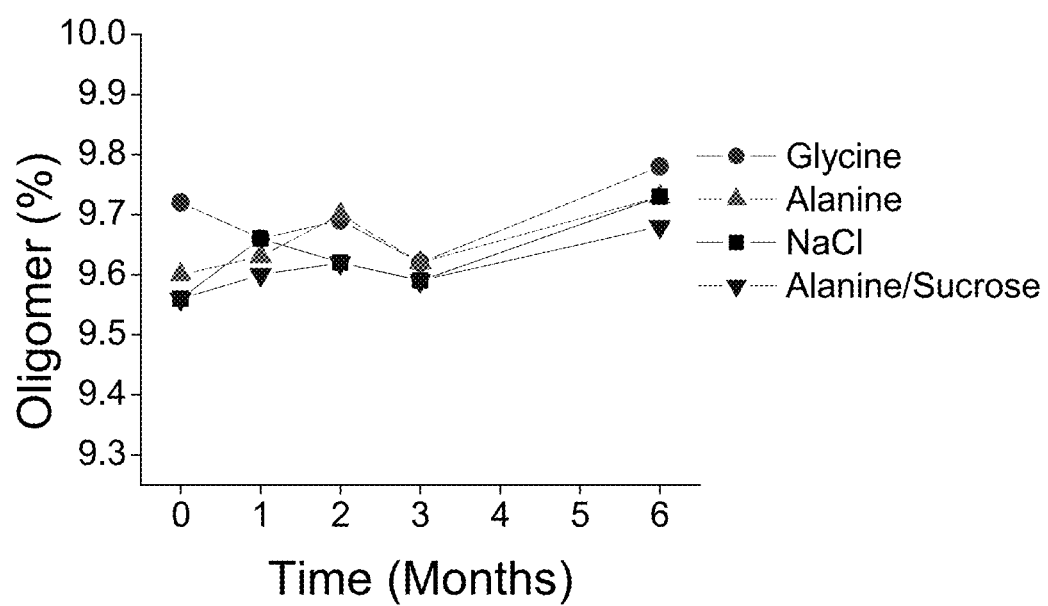
FIG. 14 is a graph showing oligomer level profiles of API formulations described in Example 6 at 5° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 15:
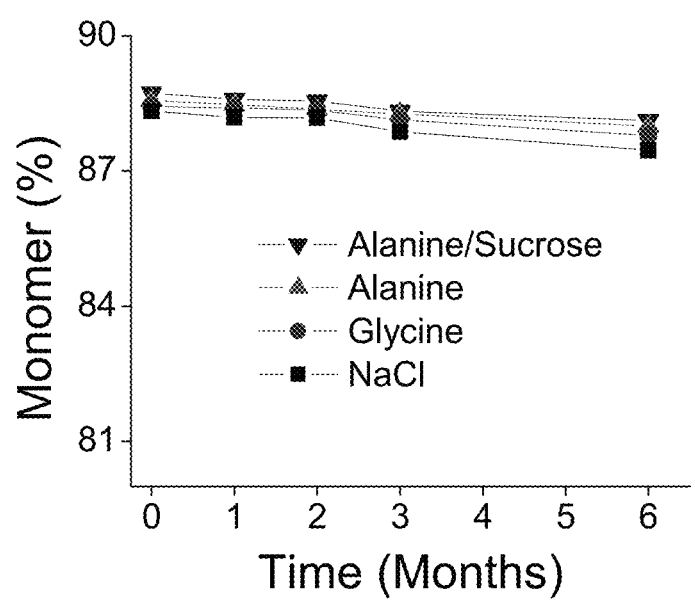
FIG. 15 is a graph showing monomer level profiles of API formulations described in Example 6 at 5° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).

According to the stability data, API formulated with NaCl (Formulation 4) displayed slightly higher aggregate level compared to other formulations as determined by SEC-HPLC. At 6 months, the aggregate level increased by 0.66%, 0.58%, 0.43% and 0.42% in NaCl (Formulation 4), glycine (Formulation 1), alanine (Formulation 2) and alanine/sucrose (Formulation 3) samples (FIGS. 12 and 13), respectively; the oligomer peaks appeared to remain unchanged (FIG. 14); and the monomer levels decreased by 0.87%, 0.61%, 0.57% and 0.65%, respectively (FIG. 15).

Figure 16:
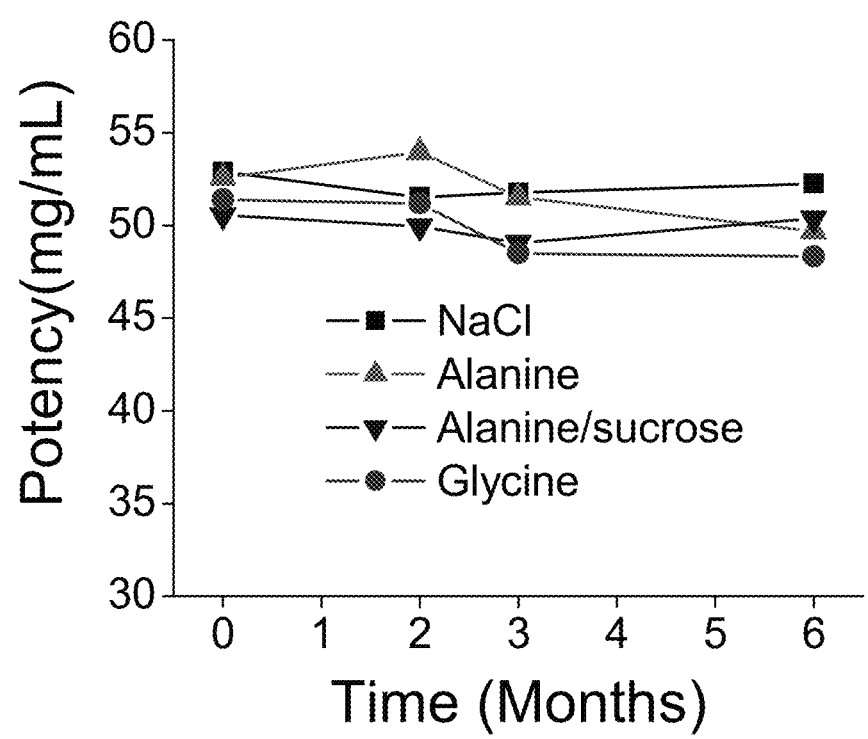
FIG. 16 is a graph showing potency profiles of API formulations described in Example 6 at 25° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 17:
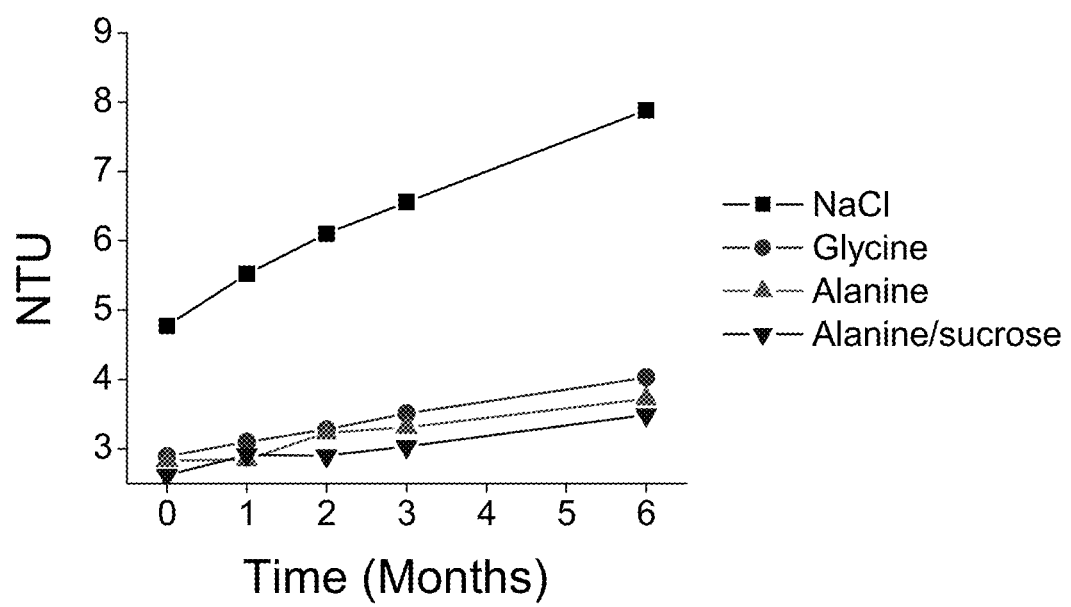
FIG. 17 is a graph showing NTU profiles of API formulations described in Example 6 at 25° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).

25° C. stability data: At 25° C., no fibril was observed in all formulations at 6 months. Little change was observed by potency (FIG. 16), pH and DLS. NTU increased with NaCl reaching the highest value 7.88 (FIG. 17).

Figure 18:
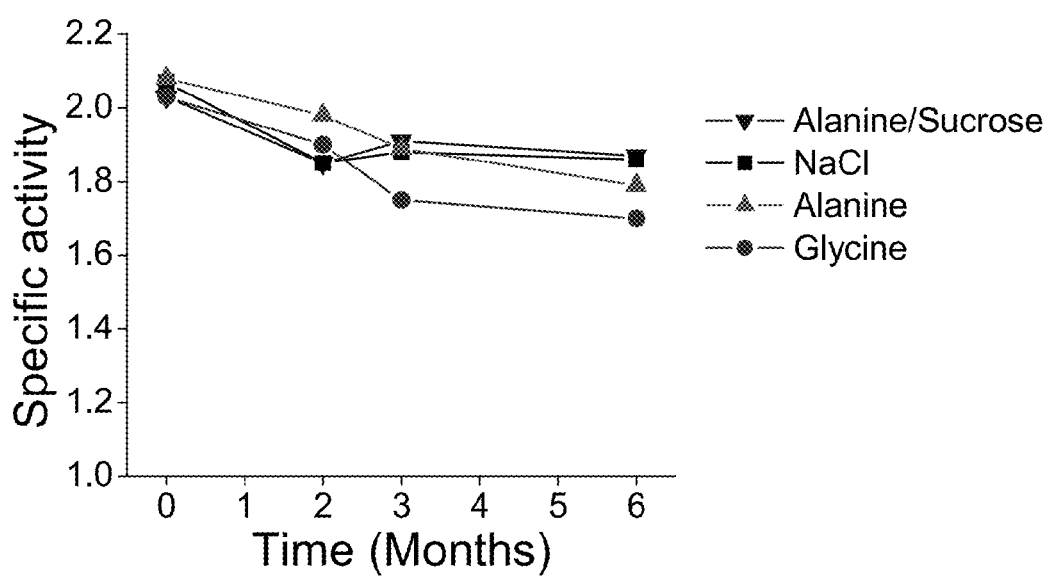
FIG. 18 is a graph showing specific activity profiles of API formulations described in Example 6 at 25° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 19:
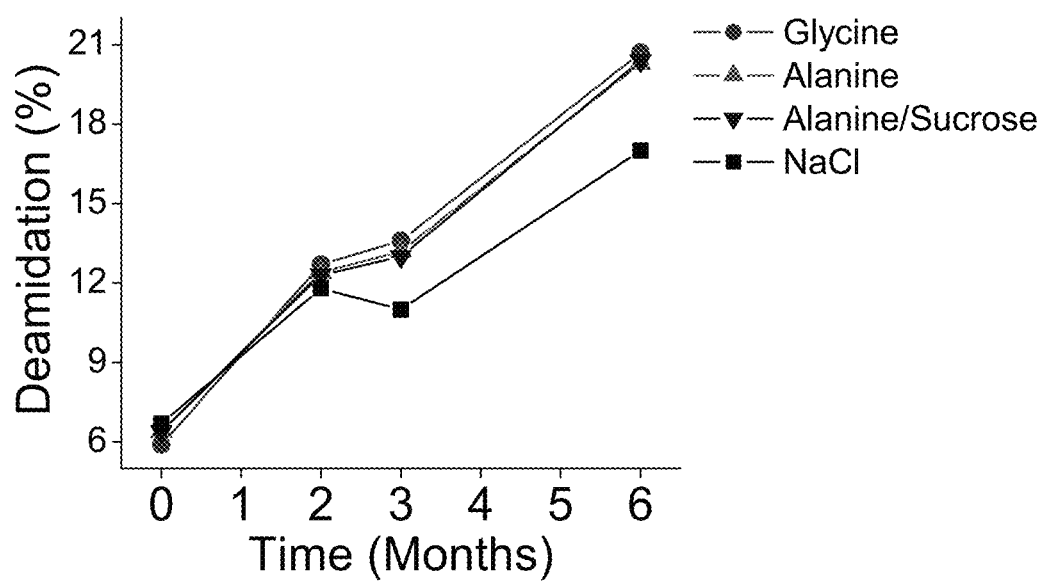
FIG. 19 is a graph showing deamidation profiles of API formulations described in Example 6 at 25° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).

The specific activity decreased by 0.2-0.3 in all formulations over 6 months (FIG. 18). This decrease can be attributed to increase in the $A_{280}$ absorbance, which increased from 25 AU to approximately 28 AU in all formulations over 6 months (FIG. 19).

Deamidation might occur in the bulk production process, which may explain the approximately 6% deamidation level of the starting material. Deamidation increased from initial average of 6% to 20% in 6 months (FIG. 19). Even though Formulation 4 exhibits slightly lower deamidation level (17%) relative to other formulations (approximately 20%), the difference is within the assay variability of 18.5%.

Figure 20:
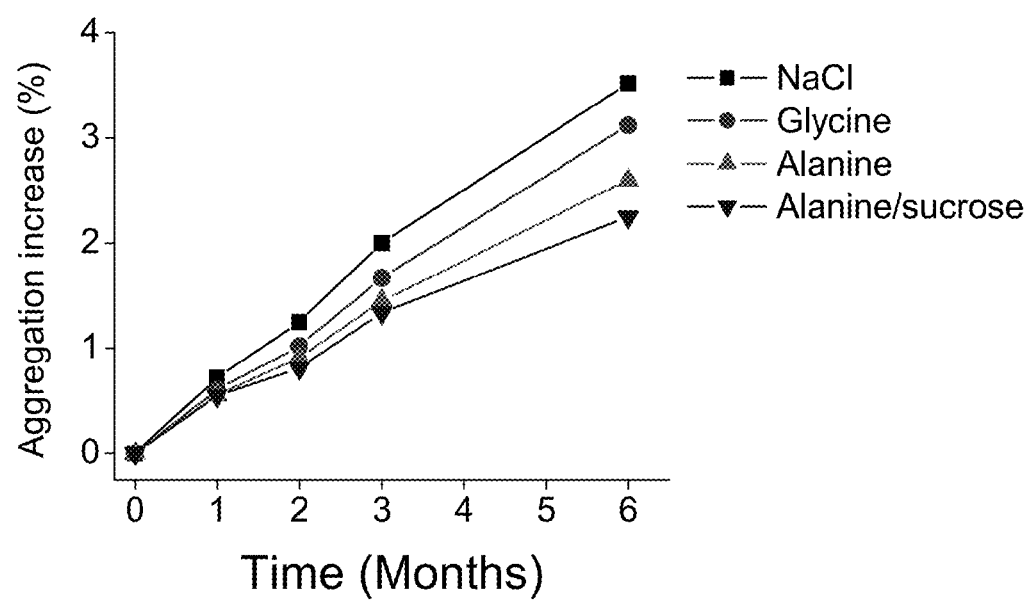
FIG. 20 is a graph showing aggregation increase profiles of API formulations described in Example 6 at 25° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 21:
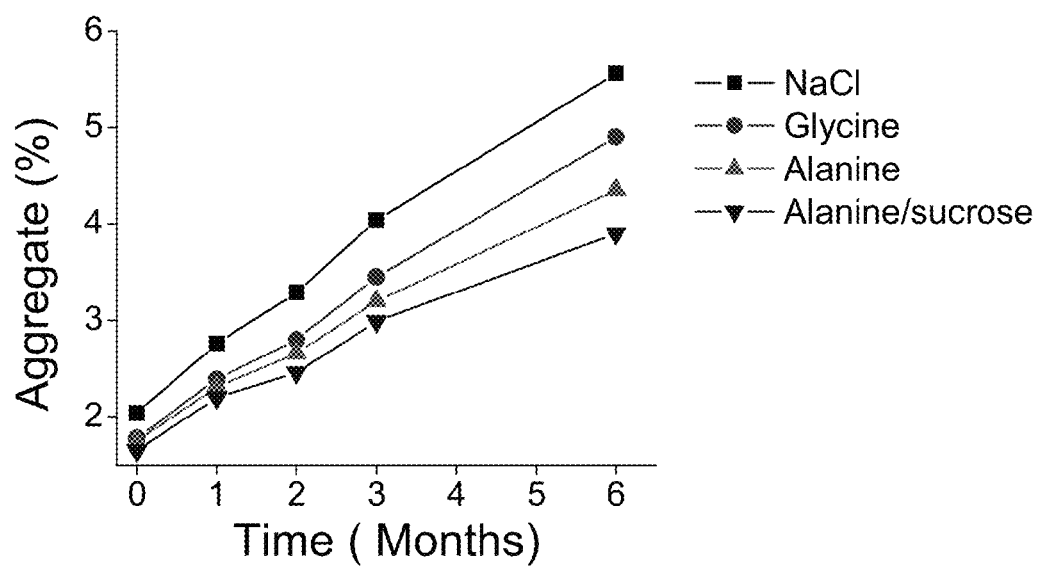
FIG. 21 is a graph showing aggregation profiles of API formulations described in Example 6 at 25° C.: "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 22:
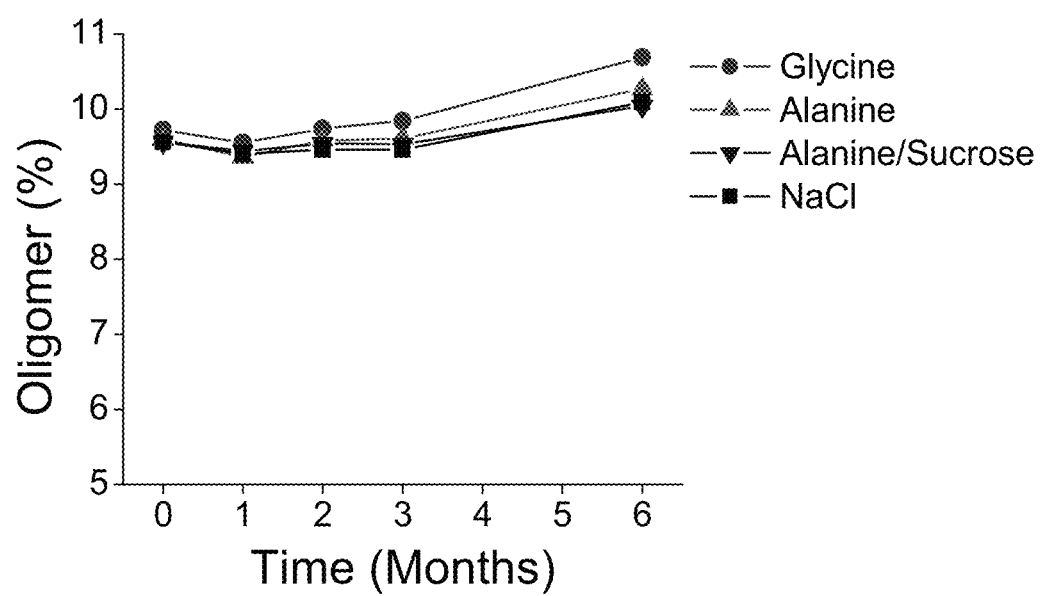
FIG. 22 is a graph showing the oligomer profile of API formulations at 25° C. "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).
Figure 23:
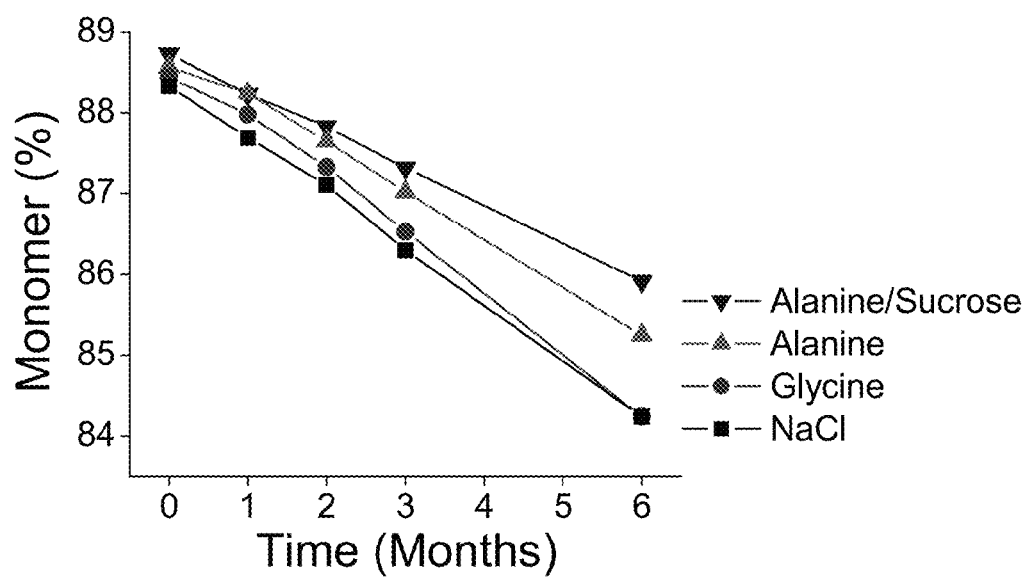
FIG. 23 is a graph showing the monomer profile of API formulations at 25° C. "Glycine" denotes Formulation 1 (API (50 mg/ml)/Glycine (250 mM)); "Alanine" denotes Formulation 2 (API (50 mg/ml)/L-Alanine (250 mM)); "Alanine/Sucrose" denotes Formulation 3 (API (50 mg/ml)/L-Alanine (125 mM)/Sucrose (125 mM)); and "NaCl" denotes Formulation 4 (API (50 mg/ml)/NaCl (250 mM)).

Aggregate level and oligomer level increased (FIGS. 21-23). Monomer levels decreased (FIG. 23) over time. The decrease in monomer level is comparable to the sum of aggregate and oligomer increase. In 6 months, the aggregate level increased by 3.52%, 3.12%, 2.6% and 2.25% in Formulation 4, Formulation 1, Formulation 2, and Formulation 3, respectively (FIG. 20).

After incubation at 5° C. for 6 months, no obvious change was observed by potency, NTU, pH, specific activity, DLS and deamidation measurements. There were slight increases (<1%) in aggregate level and corresponding decreases in monomer level. These results show stability of API formulations at 5° C. for 6 months.

Following incubation at 25° C. for 6 months, significant increase in aggregate level and NTU was observed in Formulation 4 (i.e., API plus NaCl). Glycine, alanine, and alanine/sucrose reduced aggregation and NTU with alanine/sucrose being the most effective stabilizer. Deamidation increased dramatically. These results indicate that liquid formulations comprising API are subject to aggregation and deamidation at 25° C., and that amino acids provide protection against aggregation. Extrapolation from aggregation data at 5° C. (FIG. 13) shows the predicted time to reach 5% aggregate level is ~25 months for Formulation 4, 44 months for Formulation 2, and 51 months for Formulation 3. The amino acids are therefore expected to confer significant protein stabilization, and increase shelf life substantially.

Example 7

Melting Points of Liquid Formulations Comprising API

DSC was performed to measure the transition midpoints ($T_m$) of various API formulations in order to determine their melting points.

API formulations containing API (50 mg/ml) were prepared containing various ingredients. Briefly, API solutions were dialyzed against phosphate buffers (20 mM, pH 7) containing each of the ingredients listed in Table 4. The results are shown in Table 4.

TABLE 4

Melting points of API formulations.

| Ingredient | Concentration (mM) | Melting Points (° C.) |
| --- | --- | --- |
| — | 0 | 61.54 |
| Alanine | 300 | 64.10 |
| Threonine | 300 | 64.36 |
| Hydroxyproline | 300 | 64.07 |
| Glycine | 300 | 64.43 |
| Serine | 300 | 64.37 |
| Sucrose | 300 | 64.29 |
| Glutamine | 30 | 62.13 |
| Phenylalanine | 30 | 62.02 |
| Tryptophan | 30 | 61.26 |
| Methionine | 30 | 61.32 |
| Acetyl cysteine | 30 | 63.91 |
| Leucine | 30 | 62.24 |
| Isoleucine | 30 | 62.50 |
| Valine | 300 | 62.70 |
| Lysine | 30 | 63.61 |
| Arginine | 300 | 62.88 |

The melting point of the API protein in pH 7 phosphate buffer is 61.54° C. An increase in melting point can be served as an indicator for the increase in the conformational stability of the API protein.

Example 8

Effect of pH and Protein Concentration on Liquid Formulations Comprising API

To determine the effect of pH and protein concentration on aggregation, API solutions prepared at different pH and protein concentrations were incubated at 40° C., and the aggregation data were subjected to E-CHIP analysis. The protein concentration was calculated by measuring light absorbance at 280 nm where A280/0.53 corresponds to a concentration value of 50 mg/ml. The aggregation data at 40° C. were determined for the trials listed in Table 5.

TABLE 5

Studies regarding the effect of pH and protein concentration on the aggregation of API formulations.

| Trial | API concentration (mg/ml) | pH |
|---|---|---|
| 3 | 50 | 6.3 |
| 9A | 50 | 6.7 |
| 9B | 50 | 6.7 |
| 6 | 25 | 7.1 |
| 4 | 50 | 7.1 |
| 8 | 25 | 6.3 |
| 5 | 75 | 7.1 |
| 7 | 75 | 6.3 |
| 9C | 50 | 6.7 |
| 9D | 50 | 6.7 |
| 1 | 25 | 6.7 |
| 2 | 75 | 6.7 |
| 9E | 50 | 6.7 |

Figure 24:
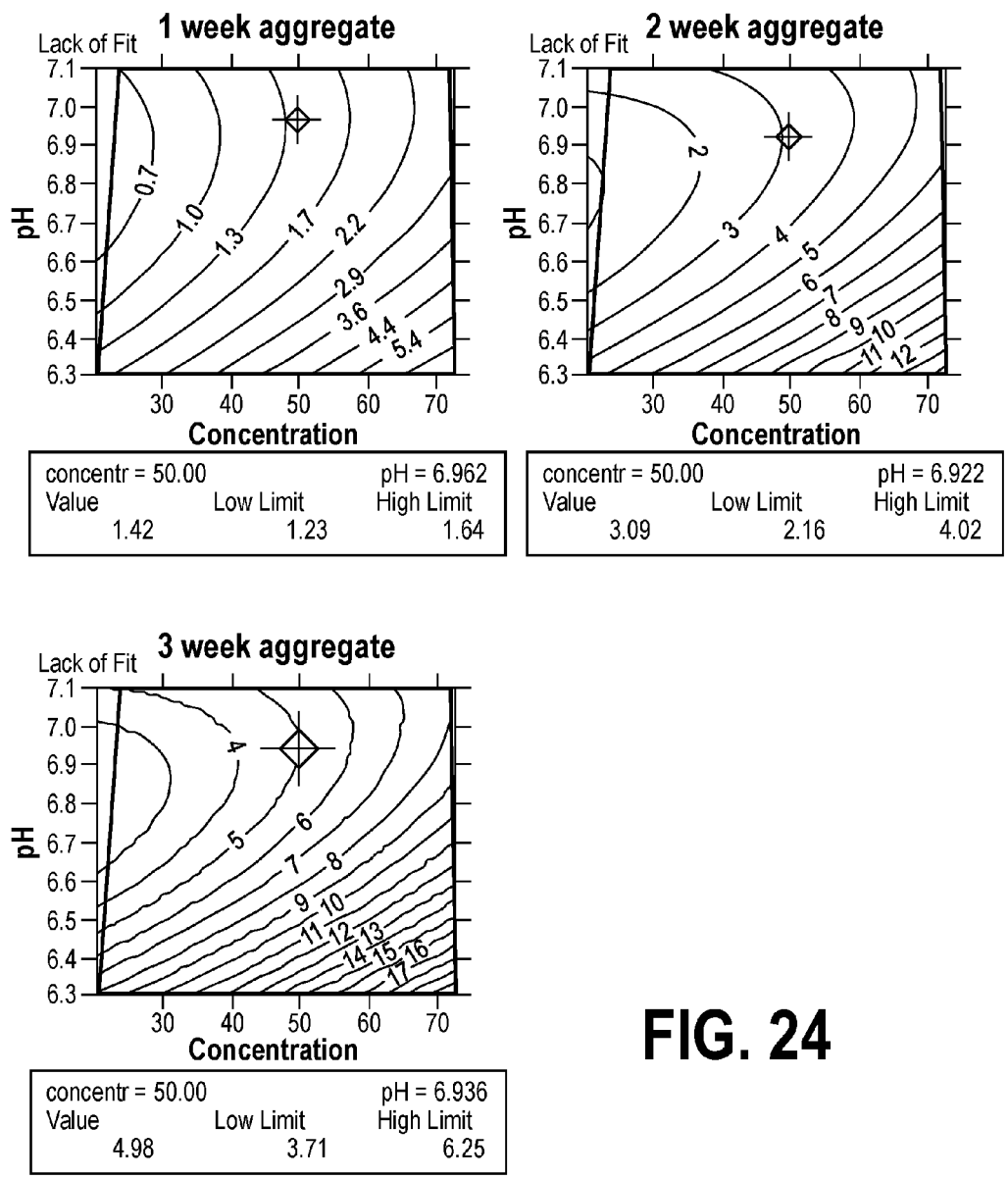
FIG. 24 is a 2D-contour plot for pH and protein concentration for 1 week, 2 weeks, and 3 weeks aggregate in an API solution at 40° C.
Figure 25:
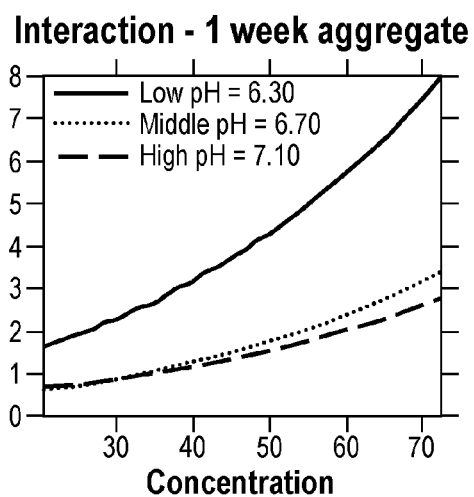
FIG. 25 is a pH and aggregation interaction plot of an API solution at 40° C. for 1 week, 2 week, and 3 weeks.
Figure 25:
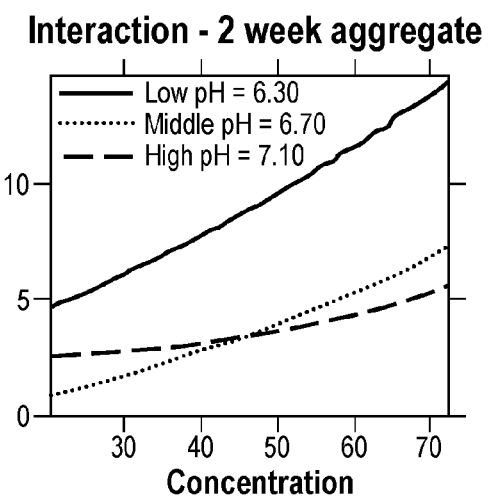
Figure 25:
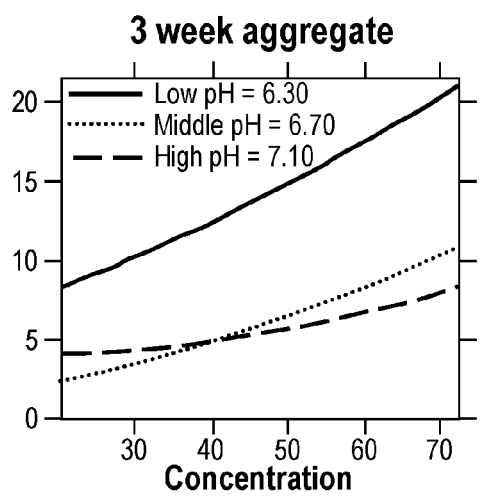
Figure 26:
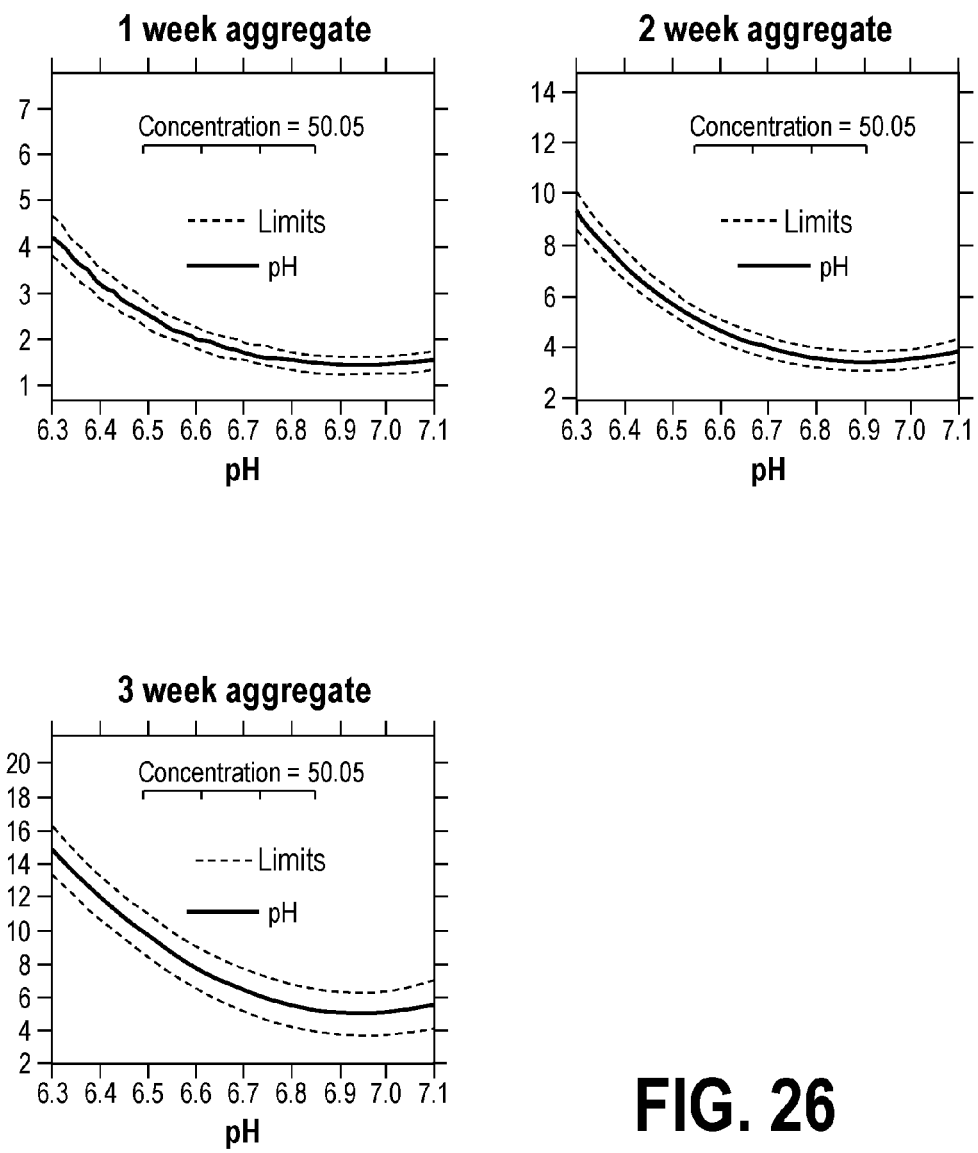
FIG. 26 shows the pH effect on aggregation in an API solution at 40° C. for 1 week, 2 week, and 3 weeks.
Figure 27:
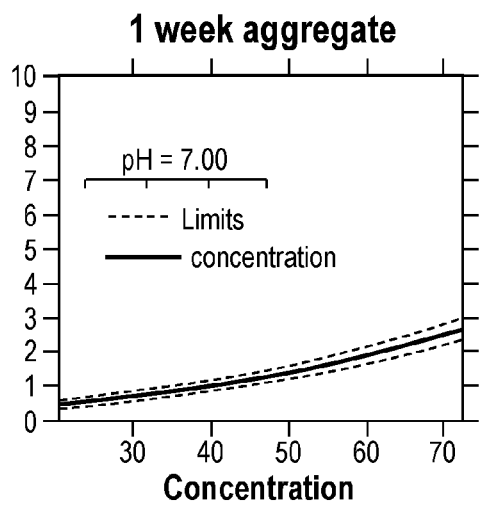
FIG. 27 shows the protein concentration effect on aggregation profile in an API solution at 40° C. for 1 week, 2 week, and 3 weeks.
Figure 27:
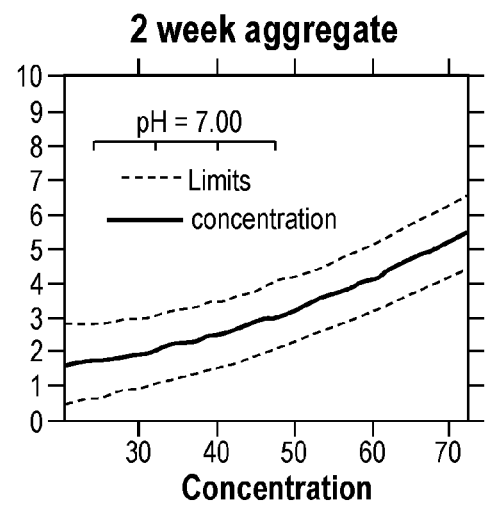
Figure 27:
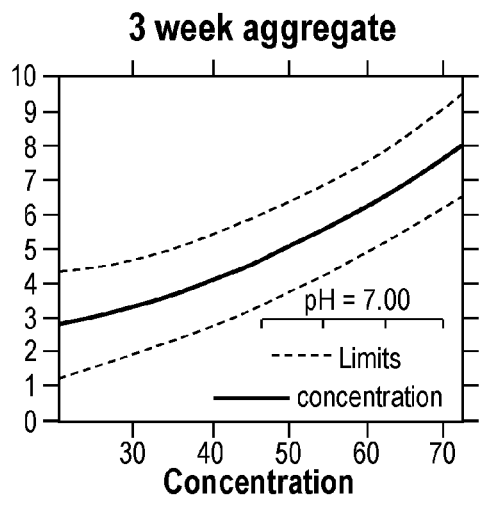

The E-CHIP model suggested the optimum pH for minimum aggregation at 50 mg/ml API is 6.9 (FIG. 24). Aggregation was observed at pH 6.3 and the aggregate amount was much less at pH 6.7 and 7.1 (FIG. 25). Aggregation decreased with the increase in pH and reached a minimum value at pH 6.9 (FIG. 26). FIG. 27 shows that the aggregation increased almost linearly with protein concentration.

We claim:

1. A stable liquid pharmaceutical composition, suitable for administration by intravenous injection, subcutaneous injection, or inhalation without reconstitution, comprising:
   (a) an alpha-1 proteinase inhibitor (API);
   (b) about 0.1M to about 0.3M alanine; and
   (c) a pharmaceutically acceptable carrier;
   wherein the concentration of API in the composition is at least about 50 mg/ml; wherein the stable liquid pharmaceutical composition exhibits less than 5% aggregation and/or degradation after at least 24 months storage at a temperature between 5° C. and 25° C.; and wherein the percent aggregation and/or degradation is determined by size exclusion high performance liquid chromatography.

2. The composition of claim 1 wherein the pharmaceutically acceptable carrier comprises:
   (a) sterile water; and
   (b) optionally, one or more buffers or excipients.

3. The composition of claim 2 wherein the one or more buffers are selected from the group consisting of, monobasic sodium phosphate dibasic sodium phosphate, and mixtures thereof.

4. The composition of claim 2 wherein the one or more excipients are selected from the group consisting of sucrose, mannitol, glycerol, sorbitol, dextran, trehalose, hydroxyethyl starch, and 1,2-propanediol.

5. The composition of claim 3 wherein the phosphate is present in an amount to maintain the solution at a pH between 6.9 and 7.1.

6. A stable liquid pharmaceutical composition suitable for administration by intravenous injection, subcutaneous injection or inhalation without reconstitution, consisting essentially of:
   (a) an alpha-1 proteinase inhibitor (API);
   (b) about 0.1M to about 0.3M alanine; and
   (c) a pharmaceutically acceptable carrier;
   wherein the concentration of API in the composition is at least about 50 mg/ml; wherein the stable liquid pharmaceutical composition exhibits less than 5% aggregation and/or degradation after at least 24 months storage at a temperature between 5° C. and 25° C.; and wherein the percent aggregation and/or degradation is determined by size exclusion high performance liquid chromatography.

7. The composition of claim 6 wherein the pharmaceutically acceptable carrier consists of:
   (a) sterile water; and
   (b) a buffer.

8. The composition of claim 7 wherein the buffer is selected from the group consisting of monobasic sodium phosphate, dibasic sodium phosphate, and mixtures thereof.

9. The composition of claim 8 wherein the phosphate is present in an amount to maintain the solution at a pH between 6.3 and 7.4.

10. The composition of claim 8 wherein the phosphate is present in an amount to maintain the solution at a pH between 6.9 and 7.1.

11. A kit comprising the composition of claim 6 suitable for intravenous or subcutaneous injection.

12. A stable liquid pharmaceutical composition, suitable for administration by intravenous injection, subcutaneous injection, or inhalation without reconstitution, consisting essentially of:
   (a) an alpha-1 proteinase inhibitor (API); and
   (b) about 0.1M to about 0.3M alanine;
   wherein the concentration of API in the composition is at least about 50 mg/ml; wherein the stable liquid pharmaceutical composition exhibits less than 5% aggregation and/or degradation after at least 24 months storage at a temperature between 5° C. and 25° C.; and wherein the percent aggregation and/or degradation is determined by size exclusion high performance liquid chromatography.

* * * * *